(12) United States Patent
Byrum et al.

(10) Patent No.: US 8,834,498 B2
(45) Date of Patent: Sep. 16, 2014

(54) METHOD AND DEVICE FOR EFFECTING ANASTOMOSIS OF HOLLOW ORGAN STRUCTURES USING ADHESIVE AND FASTENERS

(75) Inventors: Randal T. Byrum, Kings Mills, OH (US); Robert P. Gill, Mason, OH (US); William D. Kelly, Mason, OH (US); Ronald J. Kolata, Cincinnati, OH (US); Mark S. Ortiz, Milford, OH (US); Frederick E. Shelton, IV, Hillsboro, OH (US); Douglas J. Turner, Cincinnati, OH (US); James W. Voegele, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1593 days.

(21) Appl. No.: 11/558,572

(22) Filed: Nov. 10, 2006

(65) Prior Publication Data
US 2008/0114385 A1 May 15, 2008

(51) Int. Cl.
| | |
|---|---|
| A61B 17/08 | (2006.01) |
| A61B 17/11 | (2006.01) |
| A61B 17/128 | (2006.01) |
| A61B 17/122 | (2006.01) |
| A61B 17/00 | (2006.01) |
| A61B 17/115 | (2006.01) |
| A61F 2/06 | (2013.01) |
| A61B 17/064 | (2006.01) |
| A61F 2/00 | (2006.01) |

(52) U.S. Cl.
CPC ....... *A61B 17/11* (2013.01); *A61B 2017/00004* (2013.01); *A61B 17/1155* (2013.01); *A61B 2017/00893* (2013.01); *A61F 2/064* (2013.01); *A61B 17/1285* (2013.01); *A61B 2017/0641* (2013.01); *A61B 17/0643* (2013.01); *A61F 2/0063* (2013.01); *A61B 17/00491* (2013.01); *A61B 17/1114* (2013.01); *A61B 17/115* (2013.01); *A61B 2017/1107* (2013.01); *A61B 17/1227* (2013.01)
USPC .......................... 606/153; 606/142; 606/214

(58) Field of Classification Search
USPC ......................................... 606/153, 154, 151
See application file for complete search history.

(56) References Cited

U.S. PATENT DOCUMENTS

| | | | | |
|---|---|---|---|---|
| 3,974,835 | A * | 8/1976 | Hardy, Jr. ...................... | 606/154 |
| 4,055,186 | A | 10/1977 | Leveen | |
| 4,294,255 | A | 10/1981 | Geroc | |
| 4,427,737 | A * | 1/1984 | Cilento et al. ............. | 428/315.7 |
| 4,708,141 | A * | 11/1987 | Inoue et al. ................ | 227/179.1 |
| 4,766,898 | A | 8/1988 | Hardy et al. | |
| 4,874,368 | A | 10/1989 | Miller et al. | |
| 5,222,963 | A * | 6/1993 | Brinkerhoff et al. ......... | 606/153 |
| 5,254,113 | A | 10/1993 | Wilk | |
| 5,441,193 | A * | 8/1995 | Gravener ................... | 227/176.1 |

(Continued)

FOREIGN PATENT DOCUMENTS

| | | |
|---|---|---|
| WO | WO 92/09651 | 6/1992 |
| WO | WO 03/088845 | 10/2003 |

*Primary Examiner* — Dianne Dornbusch
*Assistant Examiner* — Alexander Orkin

(57) ABSTRACT

A method and devices for accomplishing the successful anastomosis of two hollow organ structures are disclosed. The method includes bringing the structures together, applying at least one fastener to hold the structures together and form a connection site, and applying, as alternatives or in conjunction, an adhesive, a wrap and/or a buttress about the connection site. Various examples of fasteners, fastener appliers, adhesives, adhesive initiators and buttress rings also are disclosed.

3 Claims, 27 Drawing Sheets

(56) References Cited

U.S. PATENT DOCUMENTS

| | | | | |
|---|---|---|---|---|
| 5,533,661 | A | 7/1996 | Main et al. | |
| 5,562,690 | A * | 10/1996 | Green et al. | 606/154 |
| 5,752,965 | A | 5/1998 | Francis et al. | |
| 5,844,087 | A | 12/1998 | Zimmerman et al. | |
| 6,283,933 | B1 * | 9/2001 | D'Alessio et al. | 604/3 |
| 6,325,810 | B1 | 12/2001 | Hamilton et al. | |
| 6,340,097 | B1 | 1/2002 | D'Alessio et al. | |
| 6,461,367 | B1 | 10/2002 | Kirsch et al. | |
| 6,503,259 | B2 * | 1/2003 | Huxel et al. | 606/153 |
| 6,666,873 | B1 | 12/2003 | Cassell | |
| 6,896,684 | B2 | 5/2005 | Monassevitch et al. | |
| 7,147,138 | B2 * | 12/2006 | Shelton, IV | 227/176.1 |
| 2002/0147462 | A1 | 10/2002 | Mair et al. | |
| 2003/0044219 | A1 | 3/2003 | Quintero | |
| 2004/0087985 | A1 * | 5/2004 | Loshakove et al. | 606/153 |
| 2004/0186490 | A1 * | 9/2004 | Gifford, III et al. | 606/153 |
| 2004/0190975 | A1 | 9/2004 | Goodman et al. | |
| 2005/0055022 | A1 * | 3/2005 | Schubert | 606/49 |
| 2005/0228446 | A1 | 10/2005 | Mooradian et al. | |
| 2006/0085032 | A1 * | 4/2006 | Viola | 606/219 |
| 2006/0135992 | A1 * | 6/2006 | Bettuchi et al. | 606/219 |
| 2008/0008744 | A1 * | 1/2008 | Prommersberger | 424/444 |

* cited by examiner

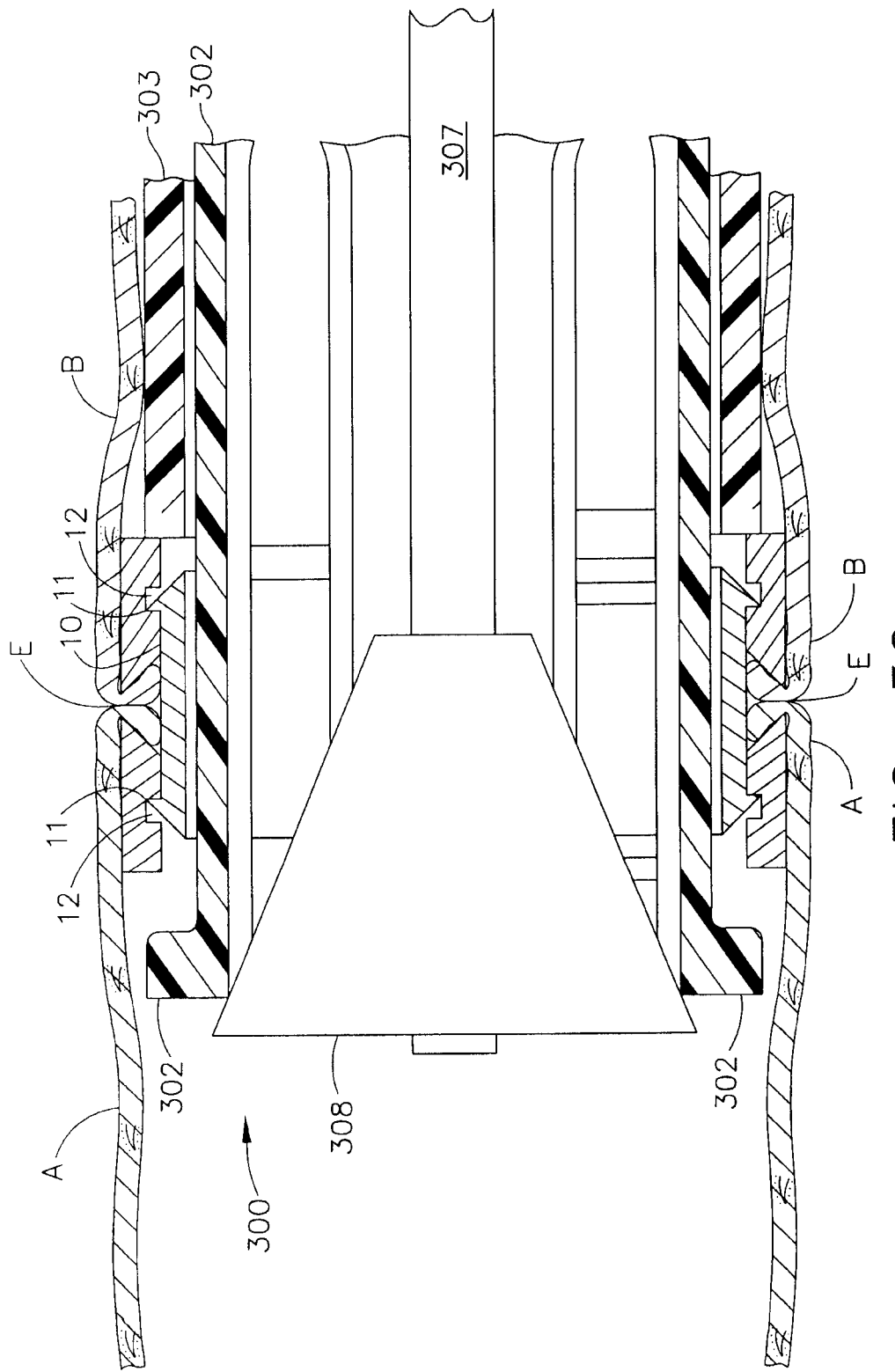

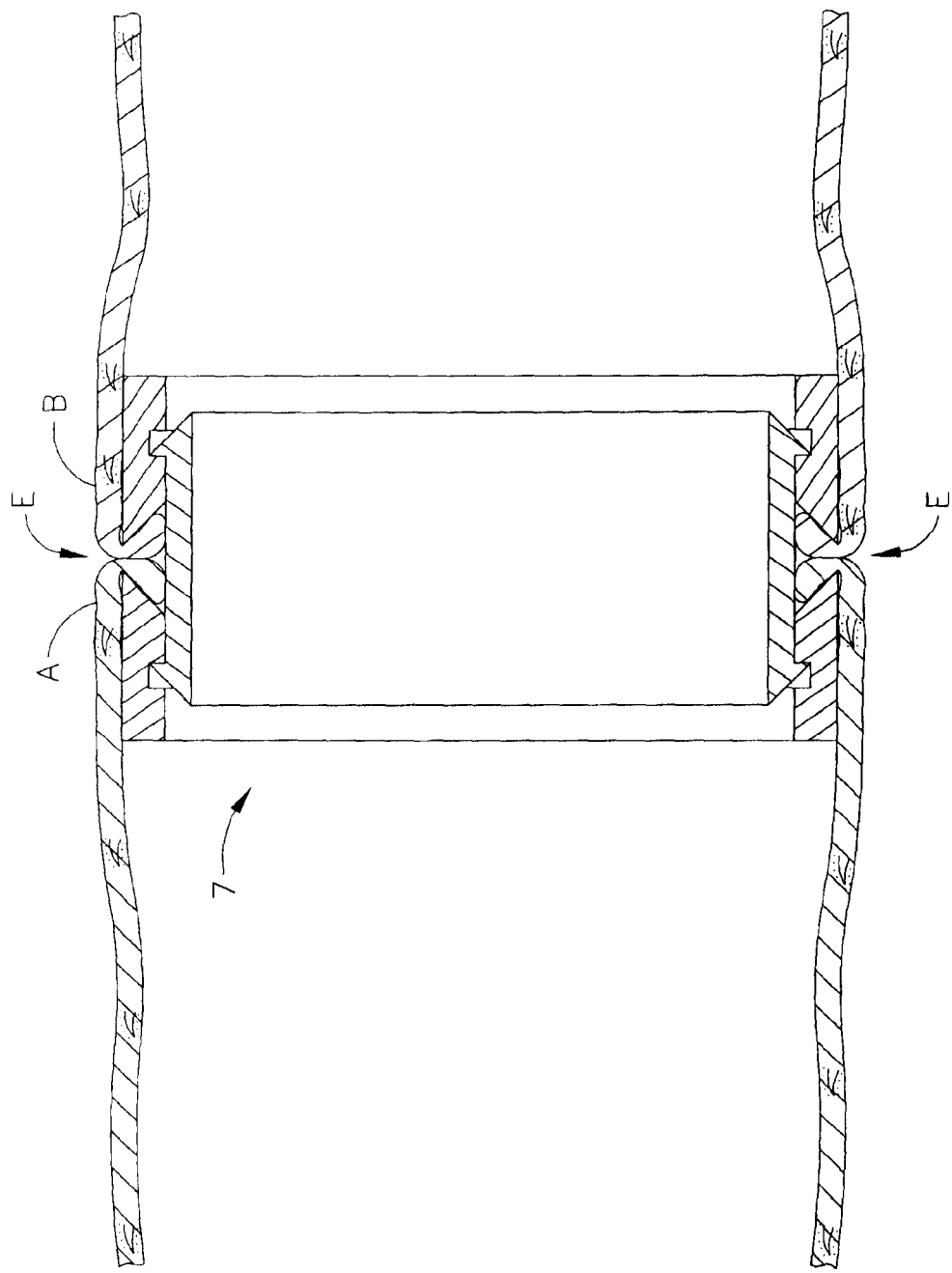

METHOD AND DEVICE FOR EFFECTING ANASTOMOSIS OF HOLLOW ORGAN STRUCTURES USING ADHESIVE AND FASTENERS

FIELD OF THE INVENTION

The present invention relates generally to surgical devices and methods for accomplishing anastomosis of respective openings of hollow organ structures, anastomosis of respective severed ends of hollow organ structures, and anastomosis of respective severed ends of intestines or colon structures.

BACKGROUND OF THE INVENTION

Connection of respective severed ends of hollow organ structures, for example, connection of severed ends of intestine or colon structures following resection of a portion thereof, to restore bodily functions, has in the past been a tedious, time consuming and difficult procedure. Because of the nature of the material that passes or is contained within some organs, such as the intestines and colon, preventing leakage from the connection (into the abdominal cavity) may be very important. Various types of circular staplers have been adopted relatively recently as an improvement over hand suturing and as a way to quickly connect respective severed ends of intestine or colon structures. Often, however, the surgeon may still be required to take steps to ensure that there are no leaks in the connection following the procedure. One technique has introducing placing dye and/or saline solution under pressure within the connected organ structures proximate to the connection site, to observe whether the connection leaks. If a leak is found, over-sewing the area in which leakage is found is a common remedial step. This may be a tedious and time consuming procedure.

There remains a need for improved devices and techniques for connecting and accomplishing anastomosis of respective hollow organ tissues, that reduce the time required for the procedure, and are effective in preventing leakage.

BRIEF DESCRIPTION OF THE DRAWINGS

The accompanying drawings, which are incorporated and constitute a part of this specification, are illustrative of particular non-exclusive examples of embodiments of the invention, and together with the description hereinbelow, serve to explain principles of the invention. In the drawings:

FIG. 32 is a longitudinal cross sectional view of the distal end of the applier shown in FIG. 27, shown after actuation has been completed to install a circumferential fastener to connect respective severed ends of hollow organ structures; and FIG. 33 is a longitudinal cross sectional view of respective severed ends of hollow organ structures connected by an installed circumferential fastener.

DETAILED DESCRIPTION OF EXEMPLARY EMBODIMENTS

As used herein, the term "proximal" (and forms thereof) means generally opposite the direction of, or away from, the distal end of an instrument, or alternatively, generally in the direction of, or toward, the proximal end of an instrument, the distal end of an instrument generally comprising the components that directly produce effects within a patient's body and the proximal end of an instrument generally comprising the components that are directly manipulated by a surgeon. As used herein, the term "distal" (and forms thereof) means generally opposite the direction of, or away from, the proximal end of an instrument, or alternatively, generally in the direction of, or toward, the distal end of an instrument, the distal end of an instrument generally comprising the components that directly produce effects within a patient's body and the proximal end of an instrument generally comprising the components that are directly manipulated by a surgeon. As used herein, the term "longitudinal" (and forms thereof) means generally along, or parallel to, the length of an instrument, including but not limited to along or parallel to the longitudinal axis of an instrument. As used herein, "transformable" means capable of being changed from a first shape, configuration or structure to a second shape, configuration or structure, including by having one or more components that are deformable, or by having a plurality of components that are movable in relationship to one another.

Figure 1:
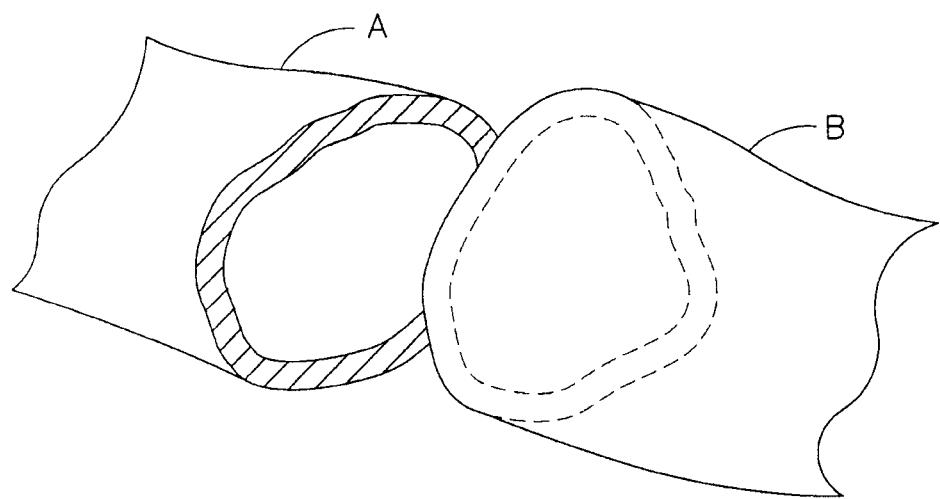
FIG. 1 is a perspective view of respective severed ends of hollow organ structures.

FIG. 1 depicts respective severed ends of hollow organ structures A and B that would be present in a patient following, for example, a therapeutic procedure involving resection of a diseased portion of a patient's intestine or bowel. In order to restore bodily functions following such a resection, the surgeon must connect severed ends A and B utilizing methods and/or devices that will effect a leakage-free connection and successful anastomosis of the structures. A successful anastomosis between particular types of hollow organ structures, such as organ structures of the bowel, may be accomplished by fastening the serosa of one structure to the serosa of the other, or by fastening the mucosa of one structure to the mucosa of the other. Both fastening arrangements are conceptually depicted in the drawings, but the scope of the invention is not limited to these.

Figure 2:
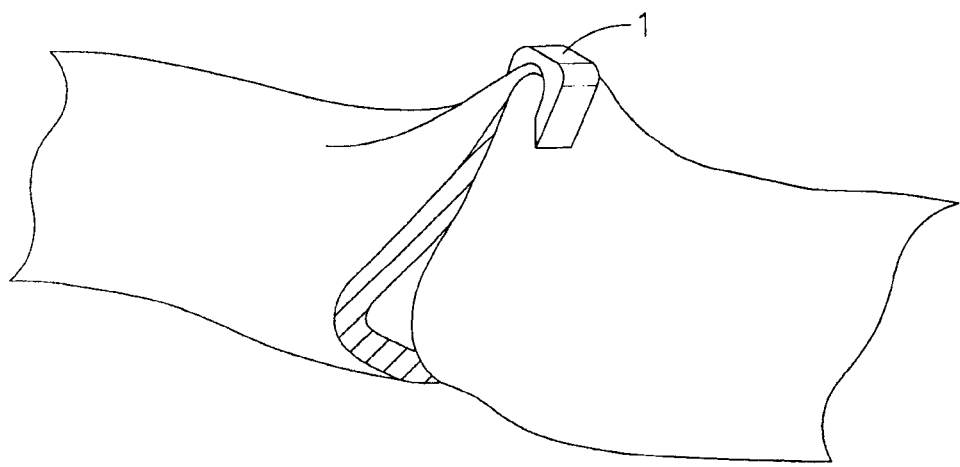
FIGS. 2 and 3 are perspective views of respective severed ends of hollow organ structures shown as they are being connected using a plurality of externally placed fasteners.
Figure 3:
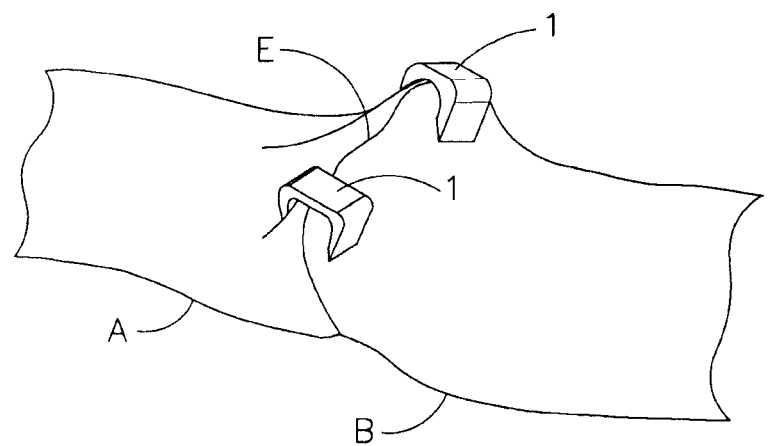

FIGS. 2 and 3 depict the respective ends of structures A and B as a connecting procedure using one possible method is in progress. Bringing and holding the respective severed ends of structures A and B together by any suitable means, the surgeon may apply fasteners 1 about the lips thereof to connect the severed ends of the structures A and B together, forming connection site E.

Figure 4:
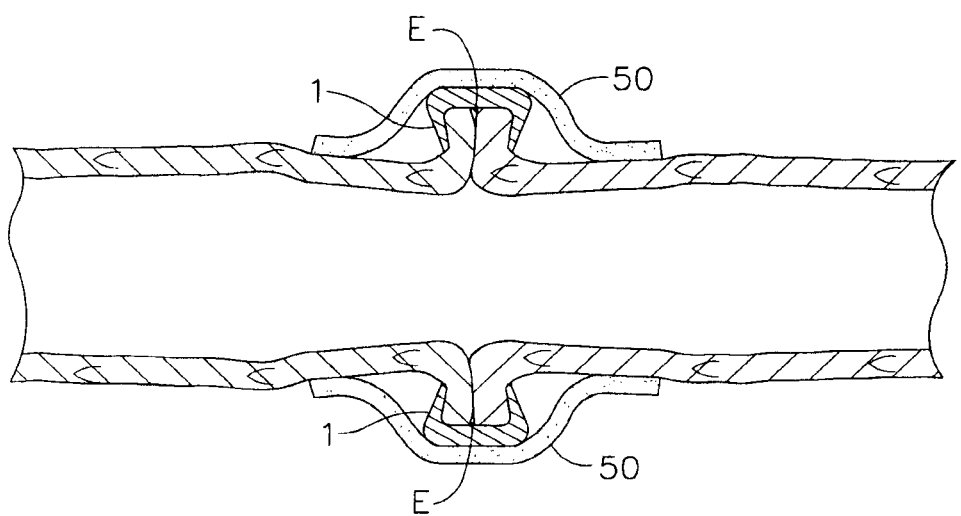
FIG. 4 is a longitudinal cross sectional view of respective severed ends of hollow organ structures shown after they have been connected by a plurality of externally placed fasteners, the connection having been covered by a wrap.
Figure 5:
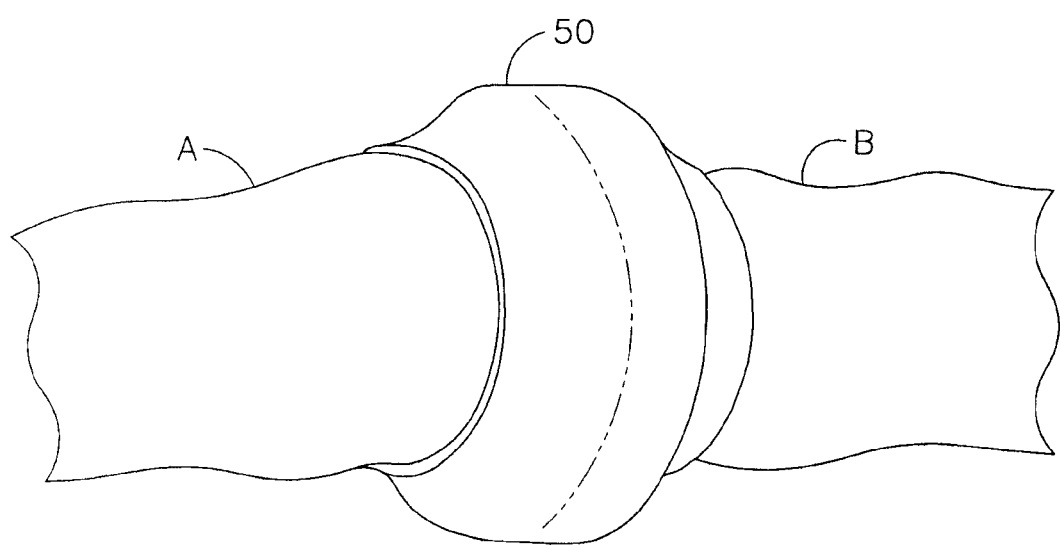
FIG. 5 is a perspective view of respective severed ends of hollow organ structures shown after they have been connected by a plurality of externally placed fasteners, the connection having been covered by a wrap.
Figure 6:
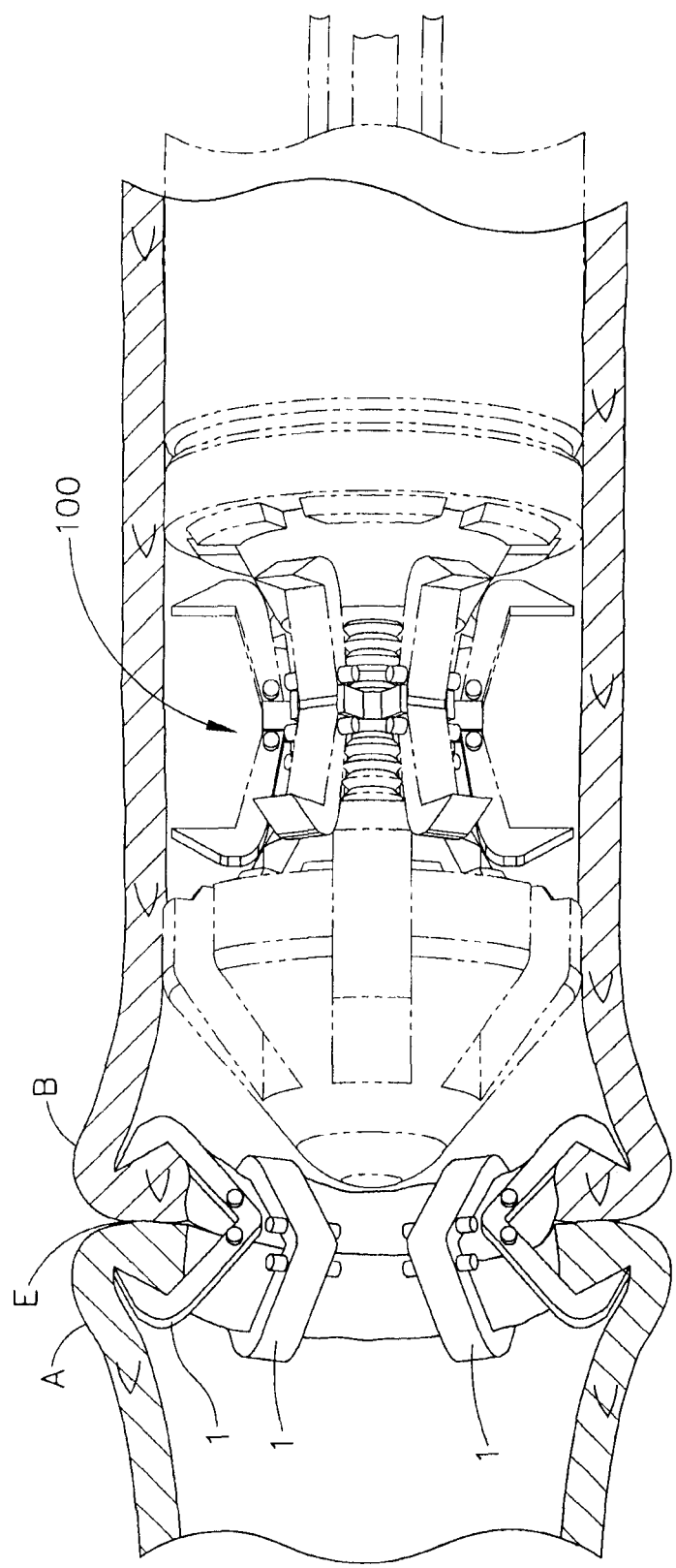
FIG. 6 is a longitudinal cross sectional view of respective severed ends of hollow organ structures shown after then have been connected by a plurality of internally placed fasteners applied using a fastener applier.
Figure 7:
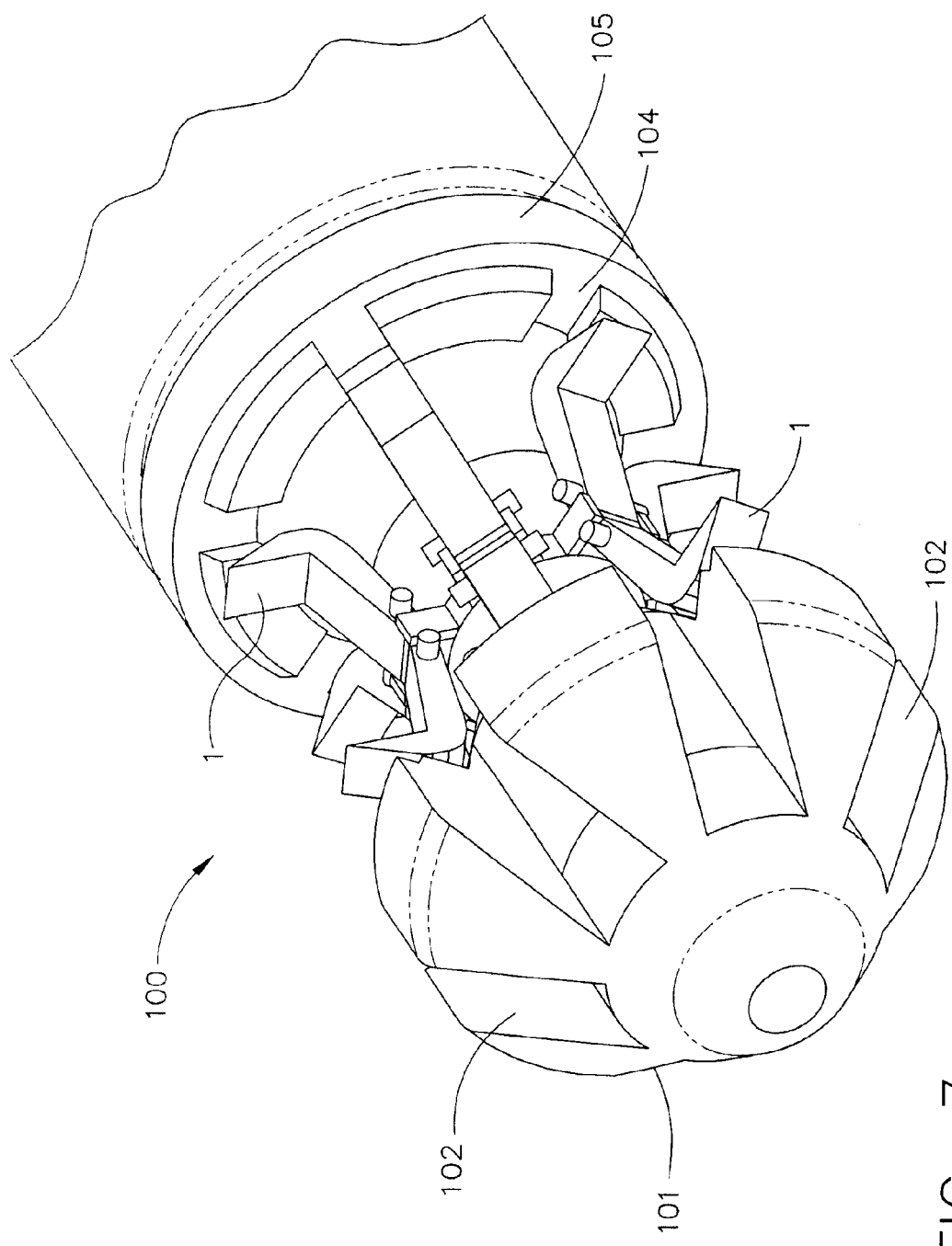
FIG. 7 is a perspective view of a fastener applier.
Figure 8:
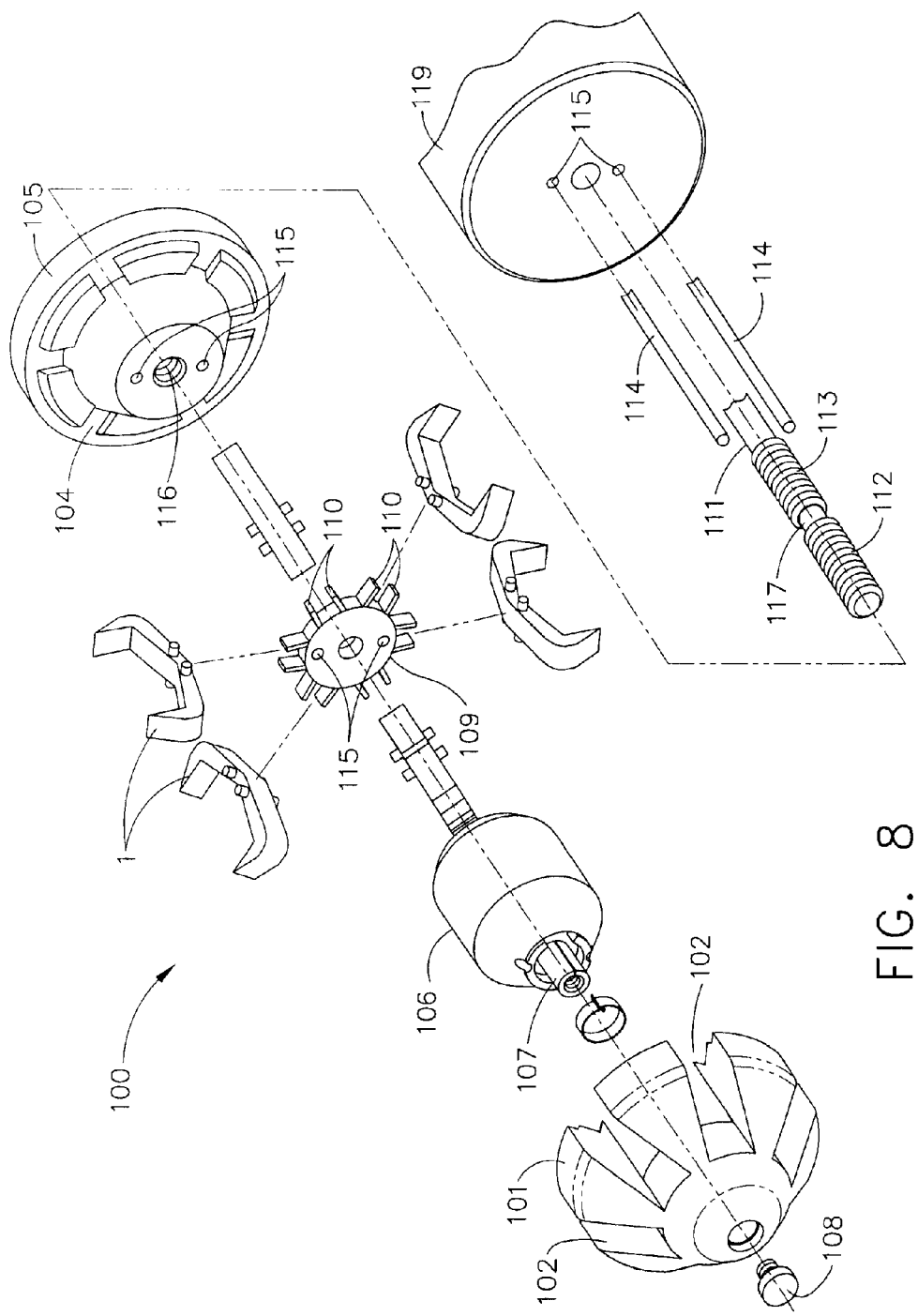
FIG. 8 is an exploded perspective view of the fastener applier of FIG. 7.
Figure 9:
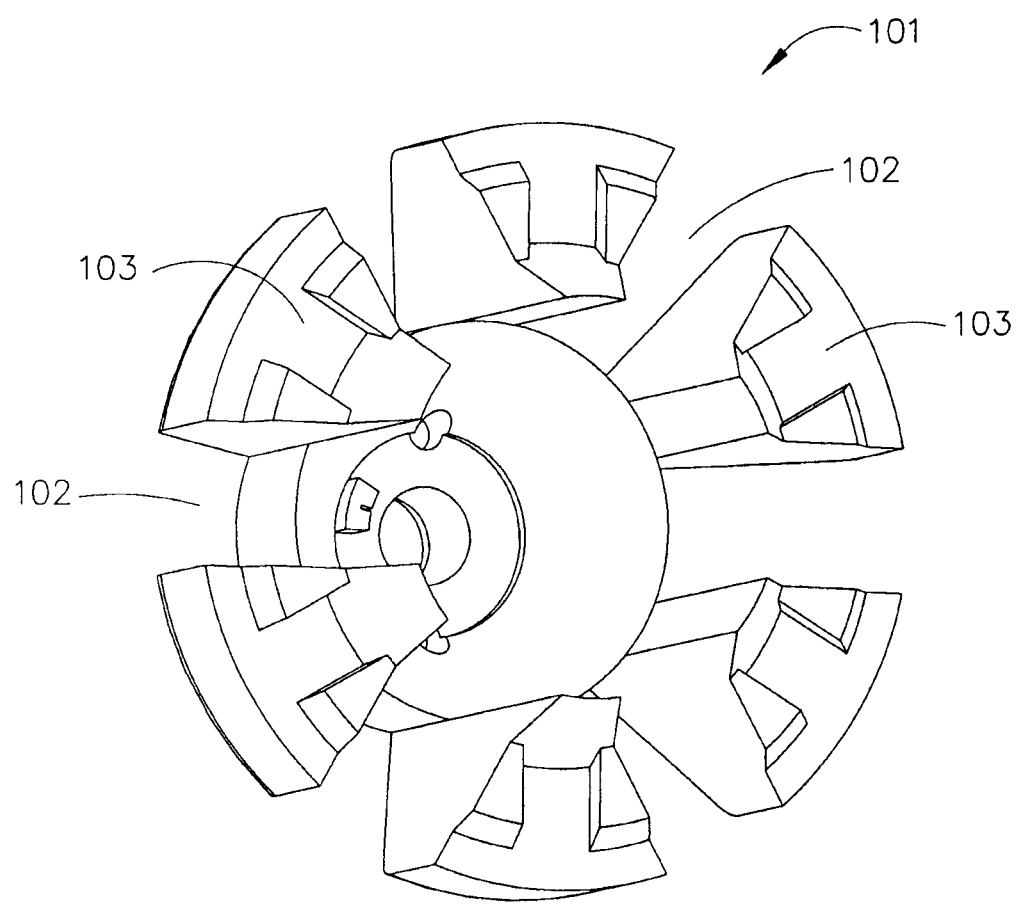
FIG. 9 is a perspective view of the nose portion of the fastener applier of FIG. 7, shown from the proximal side.

Following connecting by installation of a suitable number of fasteners 1, or use of any other suitable technique or device(s), to connect respective ends A and B, the surgeon may place a wrap 50 over a portion of, or the entire, connection site E as shown in FIG. 4. Wrap 50 may comprise any suitable biocompatible and/or bioabsorbable fabric, mesh, or porous material. Wrap 50 may comprise a continuous band, placed over either of respective ends A or B prior to the connecting thereof and then moved over the connection site following the connecting step. Alternatively, wrap 50 may comprise a discontinuous strip or tape, applied about at least a portion of the connection site following the connecting step. Wrap 50 also may comprise hydrophilic material, giving it some sticking or adhesive properties as it draws water from underlying tissues, helping it to stay in place after placement. Wrap 50 also may comprise an adhesive initiator. Following placement of wrap 50 over the connection site, the surgeon may deposit a suitable liquid or fluid adhesive over wrap 50. If wrap 50 comprises a suitable porous material, suitable liquid or fluid adhesive can wick through and about it before curing. As another alternative, wrap 50 may comprise a pre-applied dry adhesive that will be applied about the connection site by placement of wrap 50, and may be activated by, e.g. contact with water drawn from the tissues, or an initiator applied by the surgeon, and then cures. As another alternative, wrap 50 may comprise a pre-applied wet adhesive that will be applied about the connection site by placement of wrap 50, and may or may not require an initiator to cure, and following placement the surgeon may apply an initiator if required. The band, strip or tape material comprised by wrap 50 may be selected to have suitable mechanical properties so that it provides a structure and/or reinforcement matrix after curing of a suitable adhesive with which band, strip or tape material comprised by wrap 50 is coated, covered, soaked or impregnated. As a result in any of the alternatives described, a bandage encapsulating and protecting the connection site may be formed, as shown in FIG. 5. In the event a leak in the connection is detected following the application, the surgeon may re-do the application as an alternative to over-sewing.

As noted, wrap 50 may comprise, for example, a biocompatible material and may be one or more layers of a porous structure such as a gauze, an open cell foam, a mesh, or any porous structure. Wrap 50 may also comprise, for example, a bioabsorbable material such as polylactic acid, polyglycolic acid, polyglactin, polydioxanone, and polyglyconate. Additionally, wrap 50 may comprise, for example, non-absorbable materials such as metallic materials including stainless steel, titanium, or gold, or non-metallic materials including silk, nylon, polypropylene, braided polyester, polybutester, polyethylene, and polyetheretherketones (PEEK). Wrap 50 may be constructed as an absorbable strip, in layers, have non-permeable barrier layers, contain fluid absorbable or tamponade materials, and be made from any combination of absorbable or non-absorbable materials such as, by way of example, a polylactic acid and polydioxanone mix. The durometer of wrap 50 may be of any value making it soft and pliable, to firm or hard for palpability or structure (scaffolding). Wrap 50 may be pre-impregnated with or contain compounds or combinations thereof such as but not limited to adhesives, additives, and/or adhesive initiators described in greater detail below. Additionally, by way of example, wrap 50 may be adapted to increase in volume by comprising material having tamponade properties.

Additives may be combined with wrap 50. For example, wrap 50 may be coated or impregnated with an adhesive initiator such that when wrap 50 is in place, the surgeon places an adhesive onto wrap 50 and the initiator induces polymerization, setting or curing of the adhesive. Alternately, wrap 50 may be pre-coated with an adhesive and the fluid applied to wrap 50 may be an adhesive initiator that initiates or induces setting or curing of adhesive in or on wrap 50. Alternatively, by way of another example, wrap 50 may comprise radio-opaque additives such as barium and an adhesive initiator.

The adhesive may be but is not limited to polymerizable and/or cross-linkable materials such as a cyanoacrylate adhesive. The adhesive may be a monomeric (including prepolymeric) adhesive composition, a polymeric adhesive composition, or any other compound that can adhere to tissue. For example, the monomer may be a 1,1-disubstituted ethylene monomer, e.g. an alpha-cyanoacrylate. When cross linked or polymerized, the cyanoacrylate can change from a liquid to a solid. Polymerized adhesives may be formulated to be flexible to rigid. If desired, the adhesive may be a single part or dual part adhesive, and/or may contain one or more additives. Adhesive material may be selected such that curing or setting will occur through exposure to, for example, moisture, saline, body temperature, elevated temperature or an initiator.

An adhesive initiator, possibly including an accelerator, will induce polymerization and/or cross-linking and/or curing or setting of a material such as adhesive. Particular initiators for particular adhesives may be readily selected by one of skill in the art without undue experimentation. Suitable polymerization initiators and accelerators for cyanoacrylate compositions include, but are not limited to, detergent compositions; surfactants, including nonionic surfactants such as polysorbate 20 (e.g. Tween® 20; ICI Americas), polysorbate 80 (e.g. Tween® 80; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat® 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

Alternatively, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt napthenate can be used as an accelerator for peroxide. Other suitable bioactive materials are disclosed in U.S. Pat. No. 5,928,611 to Leung and U.S. patent application Ser. No. 08/920,876, filed Aug. 29, 1997, Ser. No. 09/430,176 filed Oct. 29, 1999, and Ser. No. 09/430,177, filed Oct. 29, 1999, the entire disclosures of which are incorporated herein by reference.

If desired, one or more other additives can be added or applied to the wrap 50, the adhesive or the adhesive initiator. Additives can have a number of uses such as therapeutic, medicinal, adhesion enhancers, and the like. Examples of suitable additives may include, but are not limited to, anesthetics, sclerotic or necrosing agents, plasticizing agents, thixotropic agents, buffers, catalysts, adhesive initiators, fillers, micro particles, thickeners, solvents, drugs, medicaments, stabilizers, pH modifiers, bioactive agents, cross-linking agents, chain transfer agents, fibrous reinforcements, colorants, preservatives, formaldehyde reducing or scavenging agents, mixtures thereof, and the like. Many suitable adhesives, adhesive initiators and additives may be found in United States Application 20040190975 by Goodman et al. which is hereby incorporated by reference in its entirety. Alternatively, one or more additives may be applied to the fasteners 1, buttress rings 20, 21, fastening rings 2, 5 or circumferential fastener 7 (described below).

FIGS. 6-13 depict an alternative example of a device for applying fasteners in the form of fastener applier and use thereof in an example of a method for applying a plurality of fasteners 1 to connect respective severed ends of hollow organ structures A and B. In the example illustrated, fasteners 1 connecting respective ends A and B may be installed internally, rather than externally, of the hollow organ structures.

Referring to FIGS. 7-10, the exemplary fastener applier has nose 101 having clearance grooves 102. Nose 101 may be suitably shaped to facilitate insertion into and along a hollow organ structure. Nose 101 may be affixed to block 106 by screw 108 turned into boss 107. Distal threads 112 of worm screw 111 are threaded into threaded actuation hole 118 in block 106. Worm screw 111 has distal threads 112, waist 117, about which retainer 109 rides, and proximal threads 113. Worm screw 111 has a shaft portion that emerges from base 119 and is rotatable with respect to base 119. Distal threads 112 and proximal threads 113 are cut into worm screw 111 in opposing directions (i.e., one is "right hand" thread and the other "left hand" thread, or vice versa). Seat 105 is threaded onto proximal threads 113 via threaded actuation hole 116 therein. Alignment rods 114 extend from base 119, through alignment holes 115 through seat 105 and retainer 109, and are longitudinally movable with respect thereto. Alignment rods 114 may be affixed at their distal ends within nose 101, and are longitudinally movable with respect to base 119. Deformable fasteners 1 may be releasably held by retainer 109, via retainer clips 110. Base 119 and worm screw 111 are held, and worm screw 111 may be rotated with respect to base 119, in accordance with the description of their operation below, by any suitably connected structure and mechanism located proximally of the applier.

Figure 10:
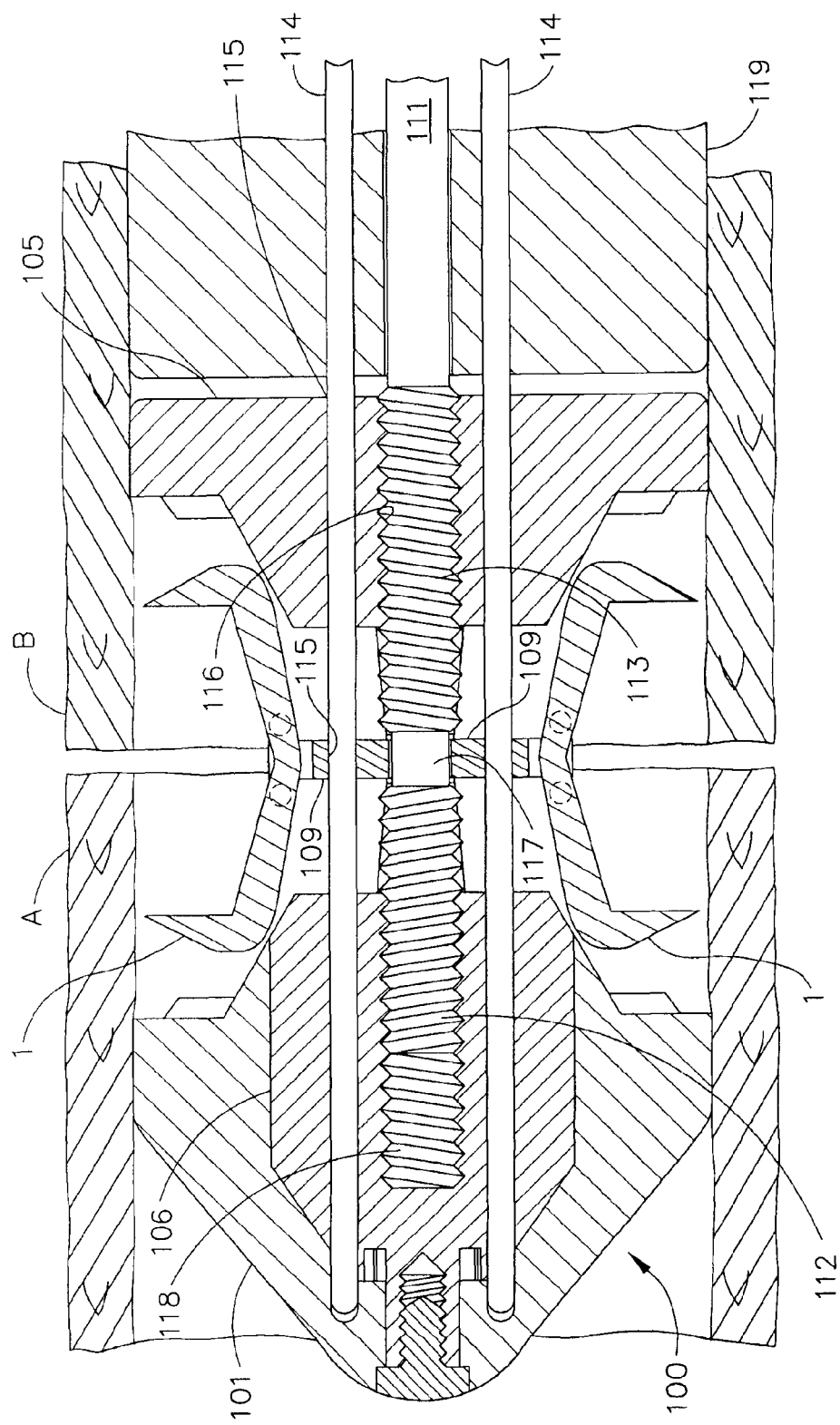
FIG. 10 is a longitudinal cross sectional view of the fastener applier of FIG. 7, shown in position ready to be actuated to connect respective severed ends of hollow organ structures.
Figure 11:
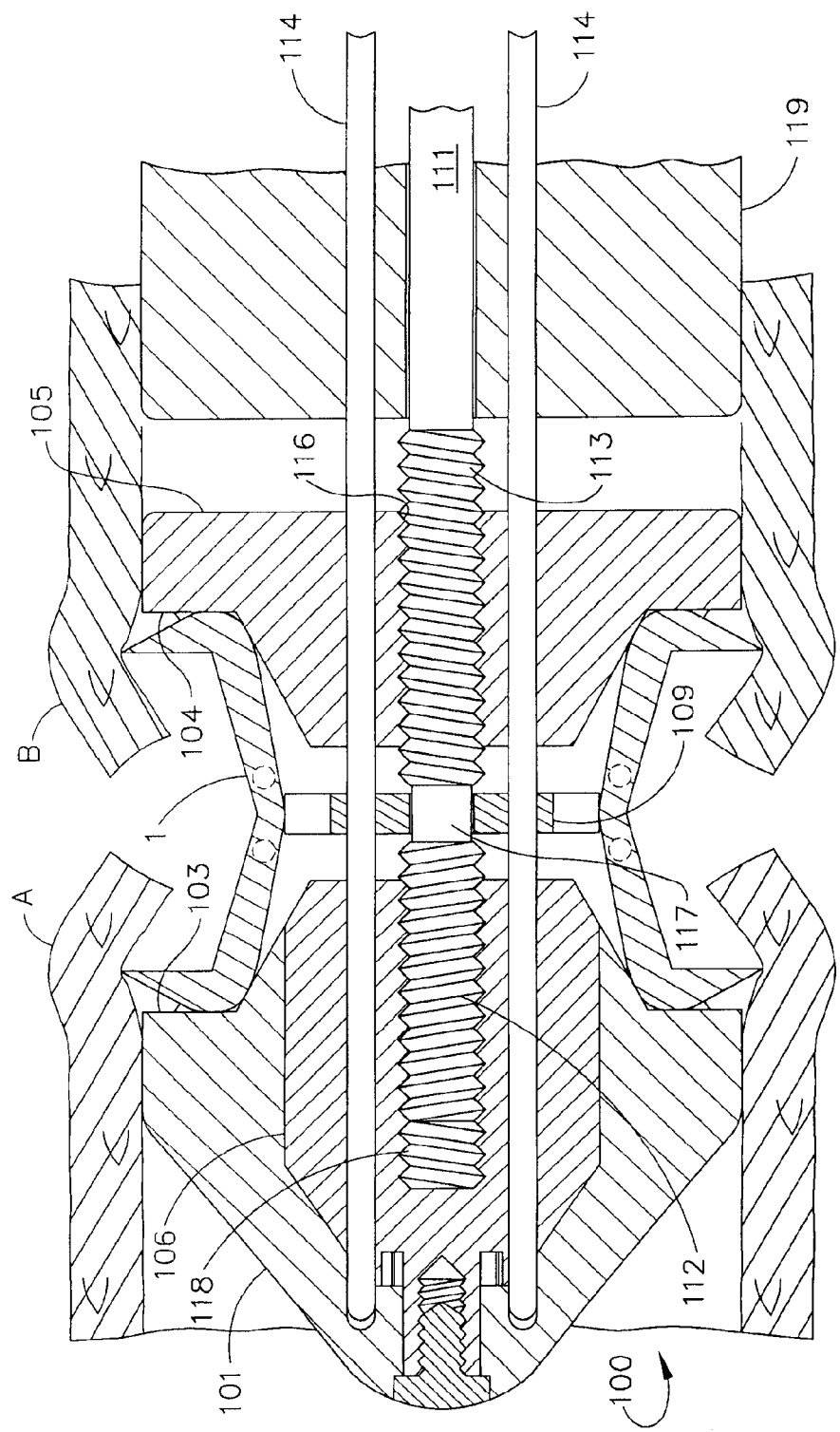
FIG. 11 is a longitudinal cross sectional view of the fastener applier of FIG. 7, shown in position to connect respective severed ends of hollow organ structures, after actuation has commenced.
Figure 12:
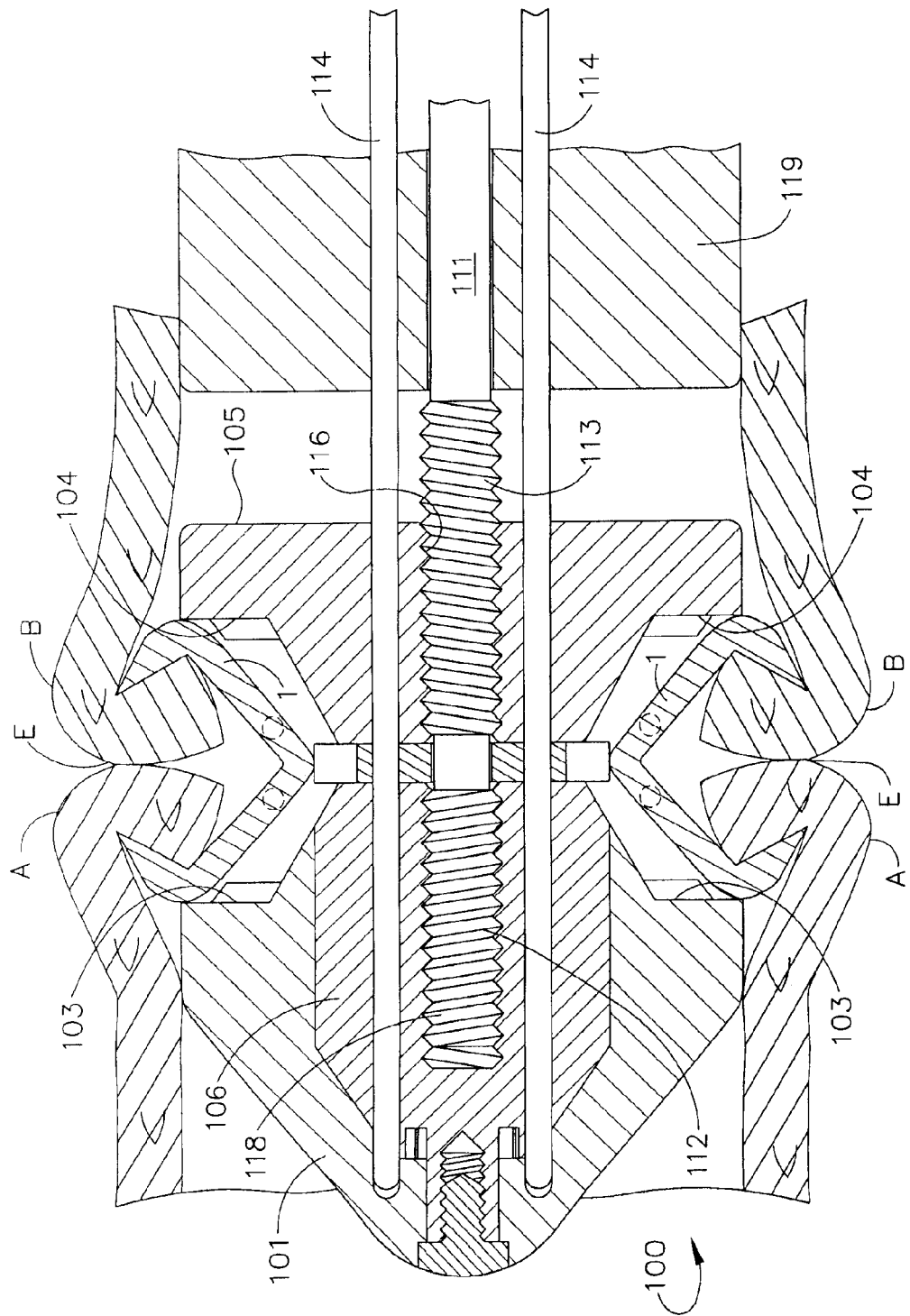
FIG. 12 is a longitudinal cross sectional view of the fastener applier of FIG. 7, shown fully actuated within respective severed ends of hollow organ structures.
Figure 13:
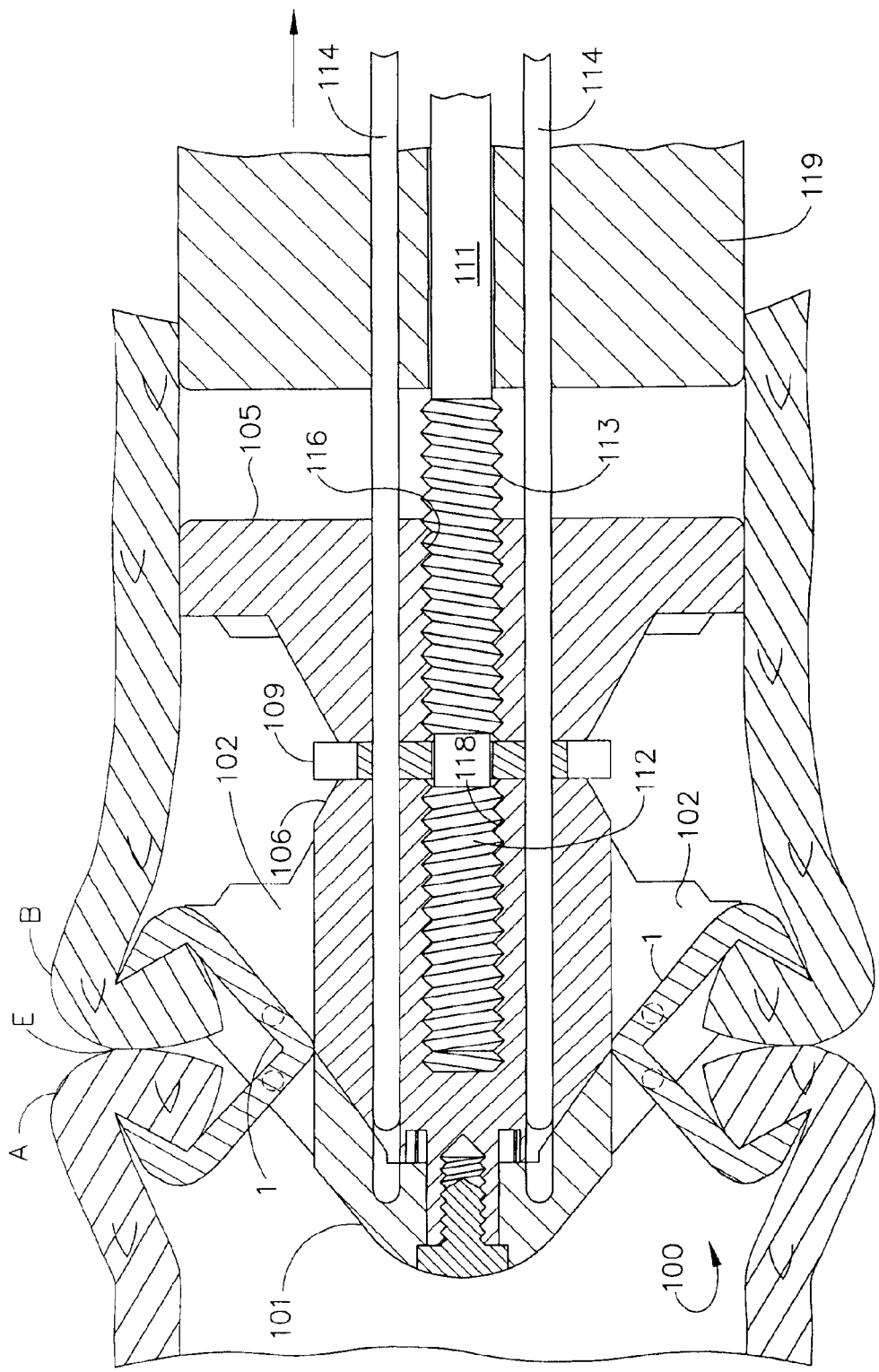
FIG. 13 is a longitudinal cross sectional view of the fastener applier of FIG. 7, shown fully actuated within respective severed ends of hollow organ structures, after withdrawal from the connection site has begun.

Use and operation of the exemplary fastener applier 100 will now be described. Referring first to FIG. 10, nose 101 of fastener applier 100 is inserted into one of the hollow organ structures at a remote location and guided therealong until it reaches, e.g. severed end B. Thereafter, it may be guided into severed end A of the other respective structure or alternatively, severed end A may be guided over nose 101, until severed ends A and B and fastener applier 100 are substantially in the positions illustrated in FIG. 10. Next, referring to FIG. 11, worm screw 111 may be turned such that distal threads 112 advance into threaded actuation hole 118 of block 106, drawing block 106 and thus nose 101 in a longitudinally proximal direction toward base 119. Because proximal threads 113 are cut into worm screw 111 in a direction opposite that of distal threads 112, this turning will correspondingly urge seat 105 in a longitudinally distal direction away from base 119 via interaction with threaded actuation hole 116 in seat 105. Block 106, nose 101 and seat 105 are prevented from rotating along with worm screw 111 by alignment rods 114. It will be appreciated that turning of worm screw 111 urges nose 101 and seat 105 longitudinally toward or away from each other, depending upon the direction worm screw 111 is turned. At the same time, retainer 109 rides on waist 117 of worm screw 111, and so does not move longitudinally but remains in place with respect to base 119, when worm screw 111 is turned. Referring to FIGS. 11 and 12 then, as nose 101 and seat 105 are drawn together by turning of worm screw 111, respective first and second anvil surfaces 103 and 104 of nose 101 and seat 105 contact fasteners 1 and deform them as shown, causing them to engage and close around the lips of the respective severed ends of hollow organ structures A and B, connecting the lips together and forming connection site E. Following installation of the fasteners 1 at the connection site, worm screw 111 may be turned in the opposite direction to cause nose 101 and seat 105 to move away from each other so as to release their grip on fasteners 1. The applier may then be rotated within the organ structure so that clearance notches 102 in nose 101 (see FIGS. 7-9) are longitudinally aligned with fasteners 1, which will allow the entire applier 100 to be withdrawn from the connection site, leaving fasteners 1 in place, as shown in progress in FIG. 13.

Fastener 1 may be formed of one or more suitable bioabsorbable and/or degradable materials, selected such that fastener 1 will break apart and/or dissolve within a suitable period of time after installation, e.g. after a period of time suitable to allow ends A and B to heal together. Such components can break apart and/or dissolve so as can be swept out of the patient's system through bodily functions, e.g. through passage of chyme material through the intestinal tract, leaving the internal passage past the connection site clear of potential obstruction created by the presence of installed objects.

Following installation of one or more fasteners to connect respective severed ends of hollow organ structures A and B as described above, connection site E may be covered by a protective wrap and adhesive combination in the manner described above and depicted generally in FIGS. 4 and 5, the only difference being that fasteners 1 may be placed alternatively on the inside, rather than the outside, of the connected organ structures.

Figure 14:
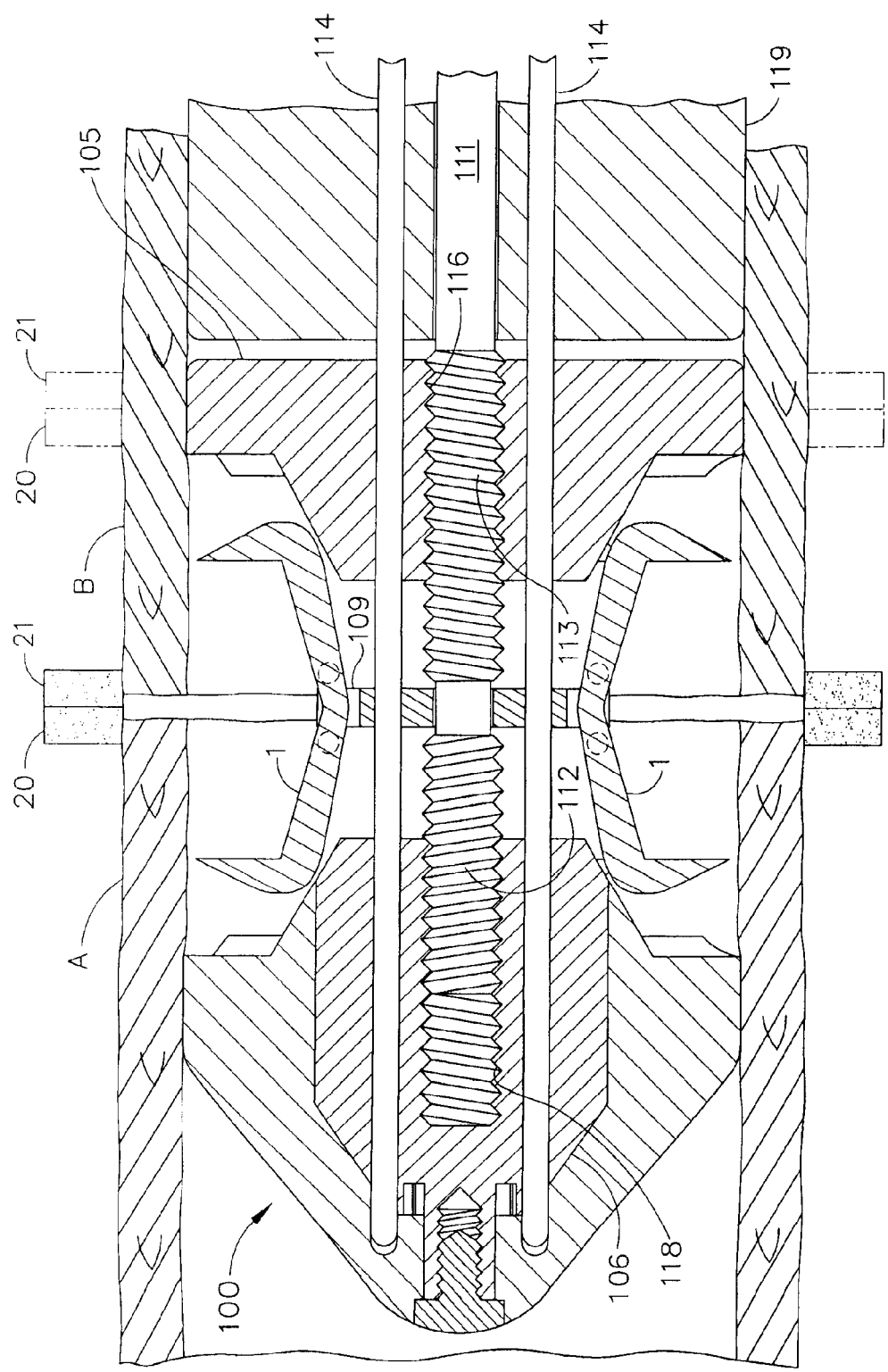
FIG. 14 is a longitudinal cross sectional view of the fastener applier of FIG. 7, shown in position ready to be actuated to connect respective severed ends of hollow organ structures, and to be used in conjunction with buttress rings.
Figure 15:
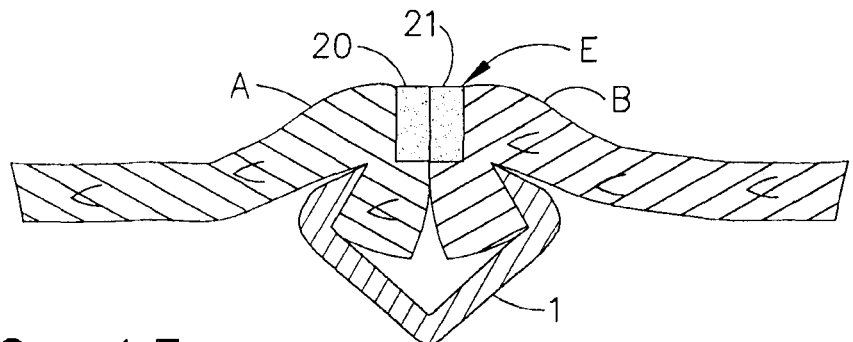
FIG. 15 is a longitudinal cross sectional view of a portion of respective severed ends of hollow organ structures, following a connecting procedure as suggested in FIG. 14.
Figure 16:
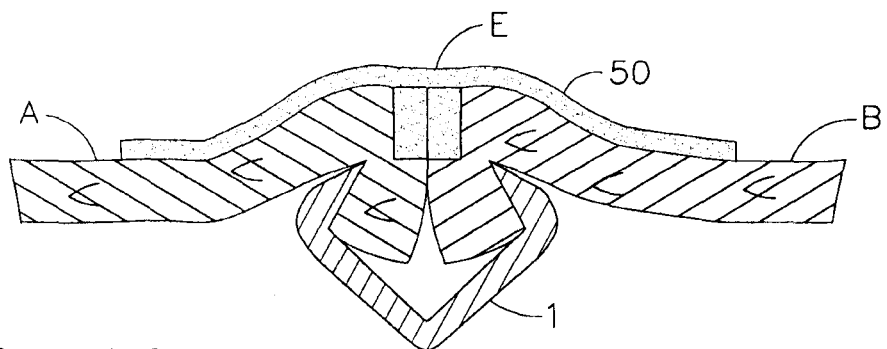
FIG. 16 is a longitudinal cross sectional view of a portion of respective severed ends of hollow organ structures, following a connecting procedure as suggested in FIG. 14, the connection having been covered by a wrap.
Figure 17:
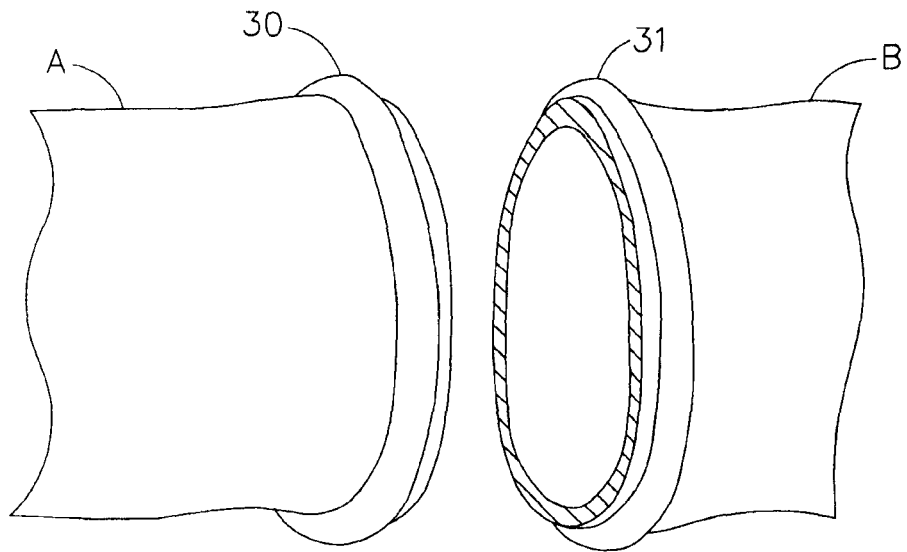
FIG. 17 is a perspective view of respective severed ends of hollow organ structures, each having a bead of adhesive material applied around its perimeter.
Figure 18:
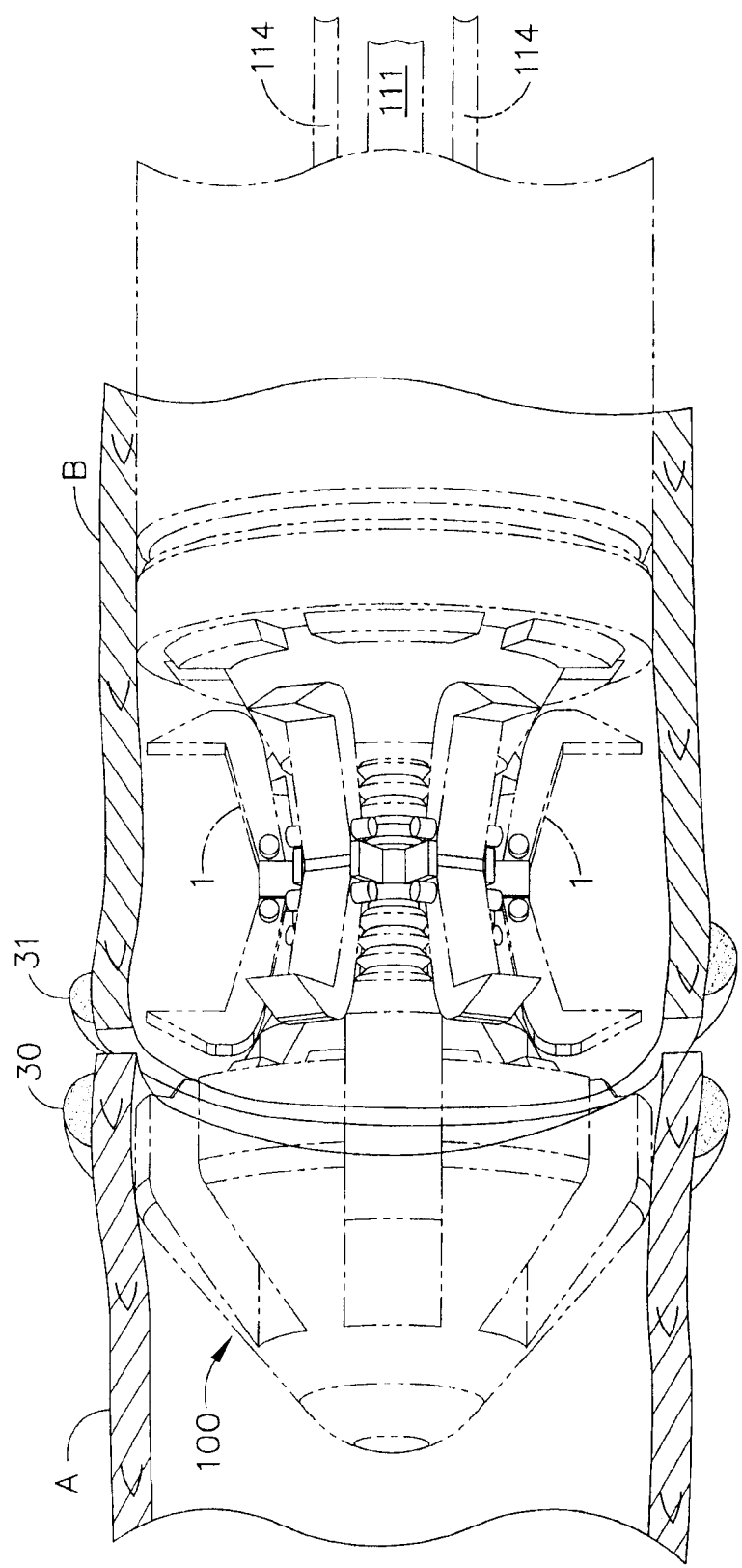
FIG. 18 is a longitudinal cross sectional view of respective severed ends of hollow organ structures, each having a bead of adhesive material applied around its perimeter, with a fastener applier such as the applier shown in FIG. 7 being inserted therein to effect a connecting of the respective ends.

FIGS. 14-16 depict another alternative example of combination of devices and method for accomplishing anastomosis of respective severed ends of hollow organ structures A and B. One or more suitably sized buttress rings 20, 21 may be placed over either of ends A or B. Next, ends A and B are brought together and an instrument, such as fastener applier 100, may be appropriately located within the structures at the connection site (see, e.g., FIG. 14). Buttress rings 20, 21 may be moved over either or both of the ends to be connected as shown. Following that the fastener applier may be actuated, resulting in a connection of the ends A and B and location of the buttress rings 20, 21 as shown in FIG. 15. The connection site E may then be wrapped with wrap 50, and suitable adhesive may be applied in conjunction therewith, in the manner described above and depicted generally in FIGS. 4 and 5, resulting in a bandaged connection depicted in FIG. 16.

A buttress ring 20, 21 may comprise any suitable biocompatible and/or bioabsorbable material, including adhesive and/or imitator that are activated and commence curing or setting after placement and connecting of the respective ends A and B. For example, one of buttress rings 20, 21 may comprise an initiator, and the other may comprise an adhesive, such that when the rings are brought together, curing or setting will commence. A buttress ring 20, 21 also may comprise a fabric or mesh, or a solid, hollow, porous or matrix structure that may contain, or be coated or impregnated with, adhesive and/or initiator and/or additive, that will be applied about the connection site when held or compressed at the connection site. A buttress ring 20, 21 may be continuous or discontinuous, for example, it may be a split ring; it may be made so as to form only a partial, or alternatively, a complete and continuous, ring; and it may have any suitable cross section and any suitable shape (i.e., it need not necessarily be circular or round, but may have, for example, an oval shape, a "C", "D" or "U" shape, or other suitable shape).

Figure 19:
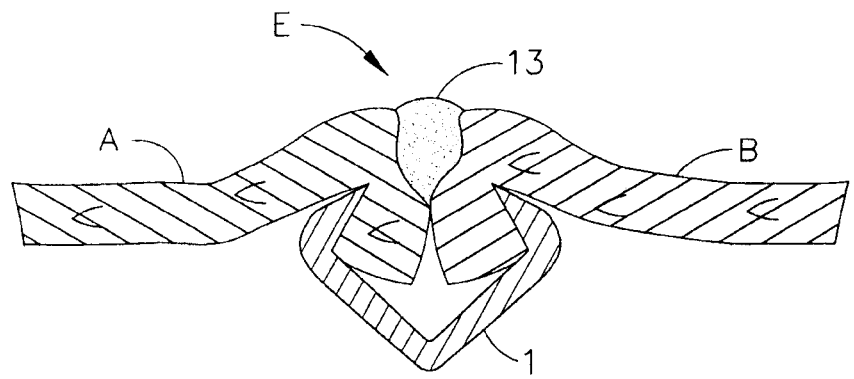
FIG. 19 is a longitudinal cross sectional view of a portion of respective severed ends of hollow organ structures, following a connecting procedure as suggested in FIG. 18.
Figure 20:
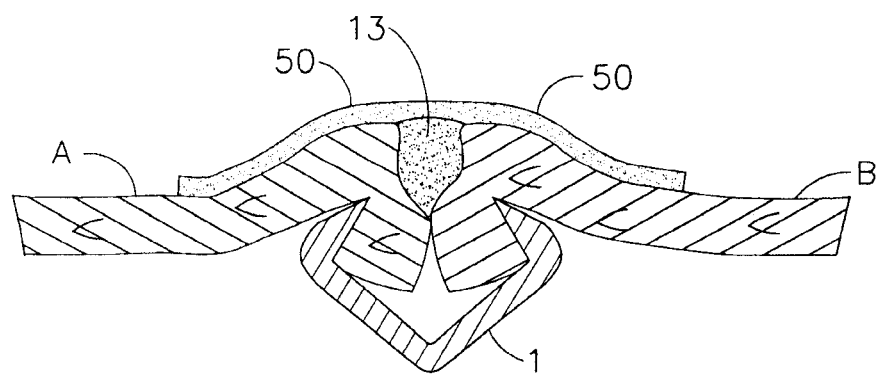
FIG. 20 is a longitudinal cross sectional view of a portion of respective severed ends of hollow organ structures, following a connecting procedure as suggested in FIG. 18, the connection having been covered by a wrap.

FIGS. 17-20 depict another alternative example of a combination of devices and method for accomplishing anastomosis of respective severed ends of hollow organ structures A and B. Beads of material 30, 31 may be placed around the edges or lips of ends A and B. Next, ends A and B may be brought together and an instrument, such as fastener applier 100, may be appropriately located within the organ structures at the connection site (see, e.g. FIG. 18). The fastener applier may then be actuated, resulting in a connection of the ends A and B and merging of the beads 30, 31 at the connection site to form an adhesive deposit 13 as shown in FIG. 19. If beads 30, 31 comprise, respectively for example, adhesive and initiator, merging of beads 30, 31 will cause commencement or curing of the adhesive to adhere and/or facilitate sealing of the connection. Alternatively, beads 30, 31 both may both comprise adhesive, or may both comprise initiator. Next, the connection site may be wrapped with wrap 50, and suitable adhesive or initiator may be applied in conjunction with wrap 50, in the manner described above and depicted generally in FIGS. 4 and 5, resulting in a bandaged connection depicted in FIG. 20.

Figure 21:
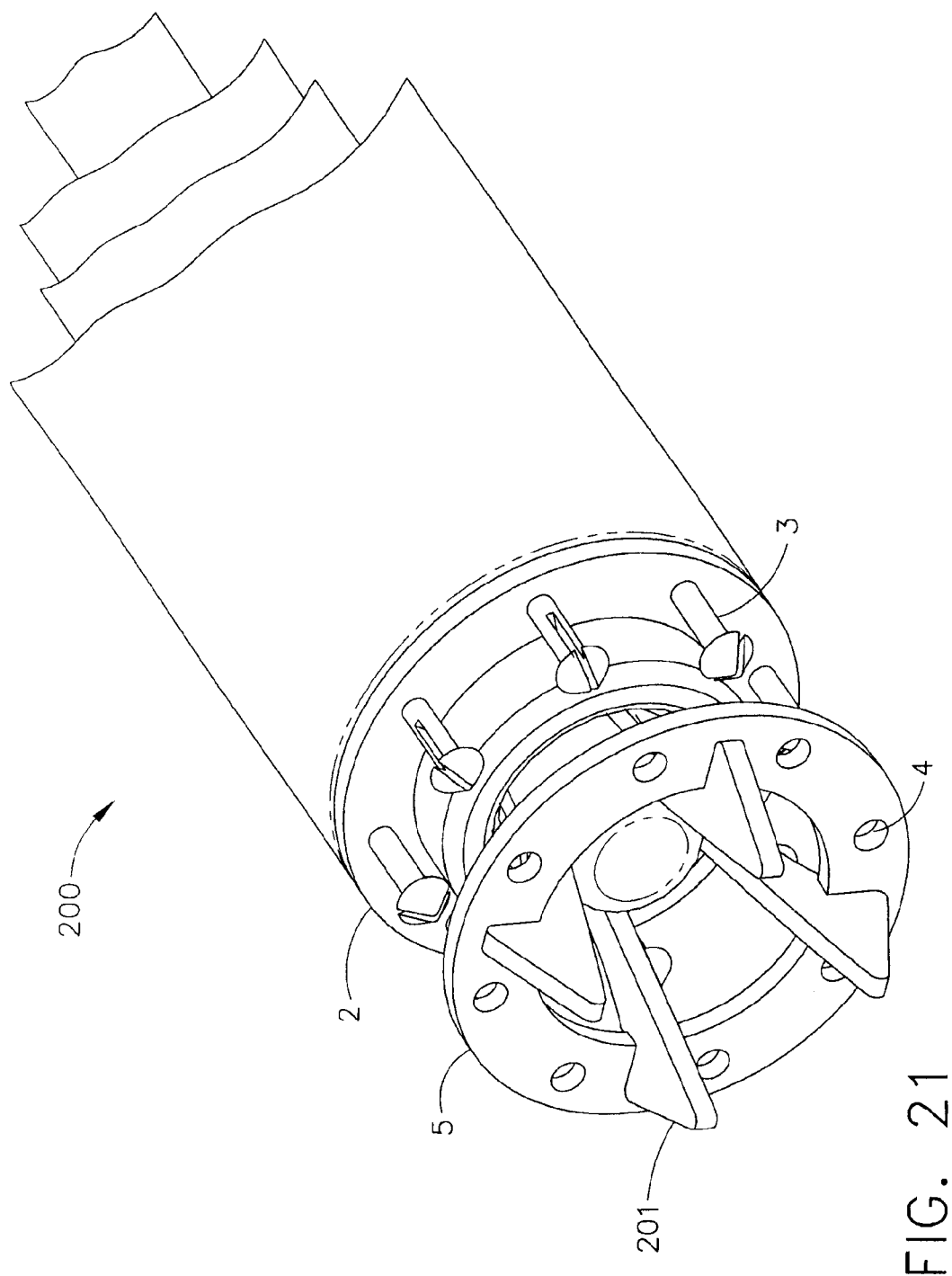
FIG. 21 is a perspective view of a fastening ring applier including the fastening ring components.
Figure 22:
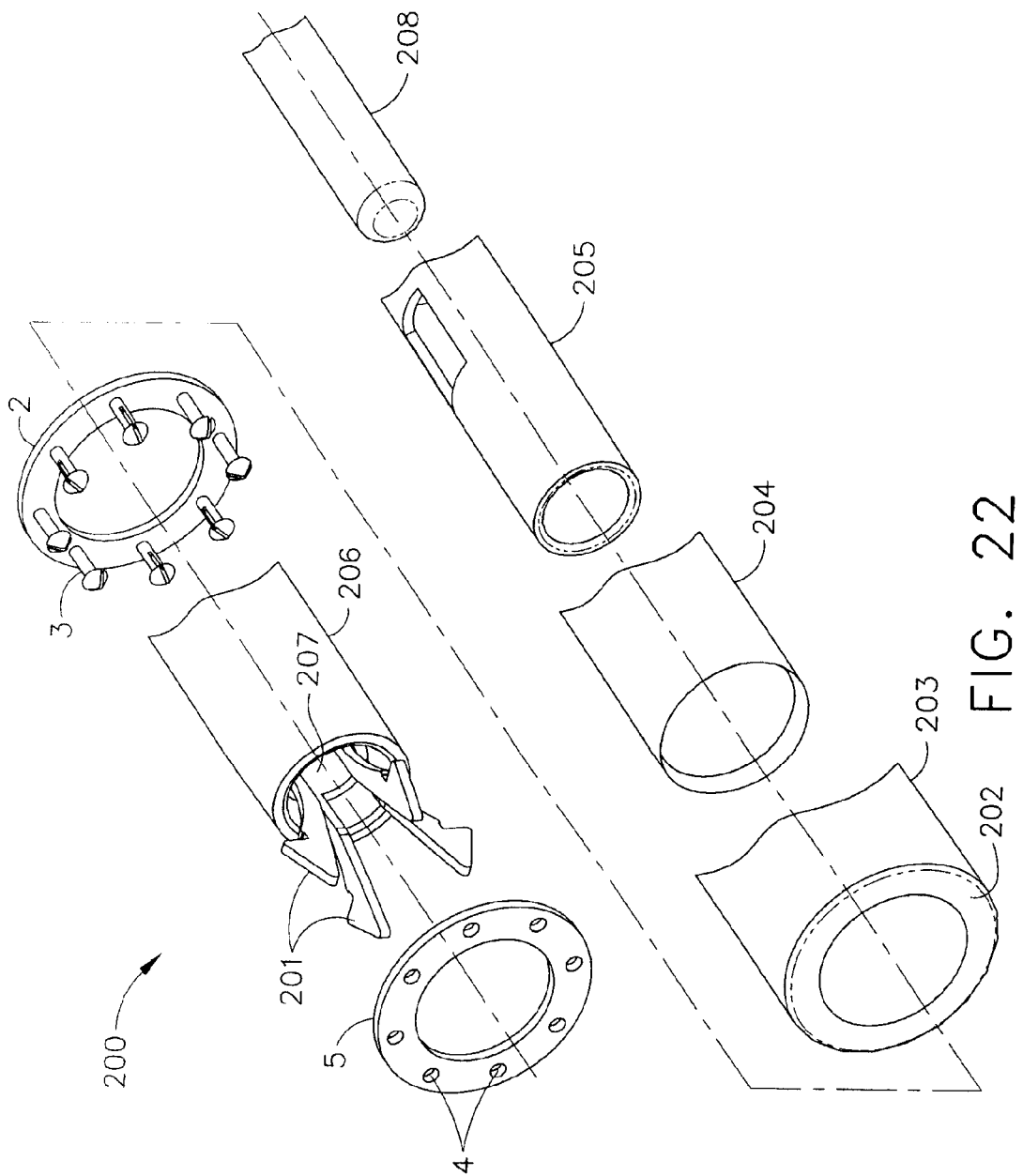
FIG. 22 is an exploded perspective view of a fastening ring applier shown in FIG. 21.
Figure 23:
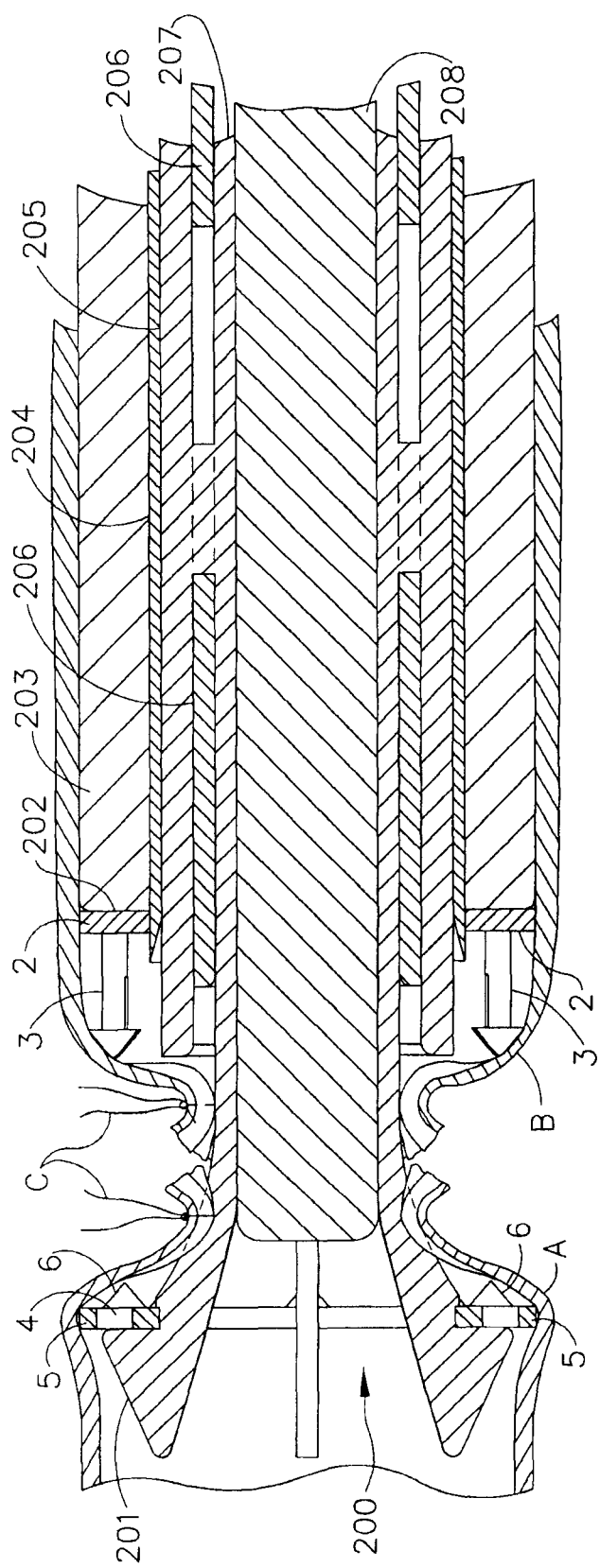
FIG. 23 is a longitudinal cross sectional view of the fastening ring applier shown in FIG. 21, shown in place within respective severed ends of hollow organ structures, and in position ready to be actuated to effect a connecting thereof.

FIGS. 21-26 depict another alternative example of a combination of devices and method for accomplishing anastomosis of respective severed ends of hollow organ structures A and B. Referring to FIGS. 21-23, fastening ring applier 200 may be made operable to apply a fastener comprising a pair of fastening rings 2, 5 releasably held by flexible fingers 201. Proximal fastening ring 2 may comprise a plurality of connecting members 3, which may have pointed heads as shown, and may have features that are flexible so as may deform to cooperate with suitably formed holes 4 or other cooperating connecting features comprised by fastening ring 5 that cooperate with connecting members 3, and effect connection therein or thereto. Either or both of proximal fastening ring 2 and distal fastening ring 5 may comprise a plurality of projections 6 or other features formed to, e.g. enhance gripping of tissues, facilitate or restrict circulation in fastened tissues, affect the shape of the connection site, etc. Proximal fastening ring 5 rests against ring seat 202, at the distal end of seat tube 203. A cutter tube 204 may be located within seat tube 203; a main tube 205 may be located within cutter tube 204; a retractor tube 206 may be located within main tube 205; a finger tube 207 may be located within retractor tube 206 and connected to fingers 201; and a spreader 208 may be located within finger tube 207. Respective tubes 203, 204, 205, 206, 207 and 208 may be held and/or longitudinally moved with respect to each other to effect operation as will hereinafter be described, by any suitably connected structure and mechanism located proximally of the applier. Cutter tube 204, if included, may have a suitably sharpened distal end as shown.

Figure 26:
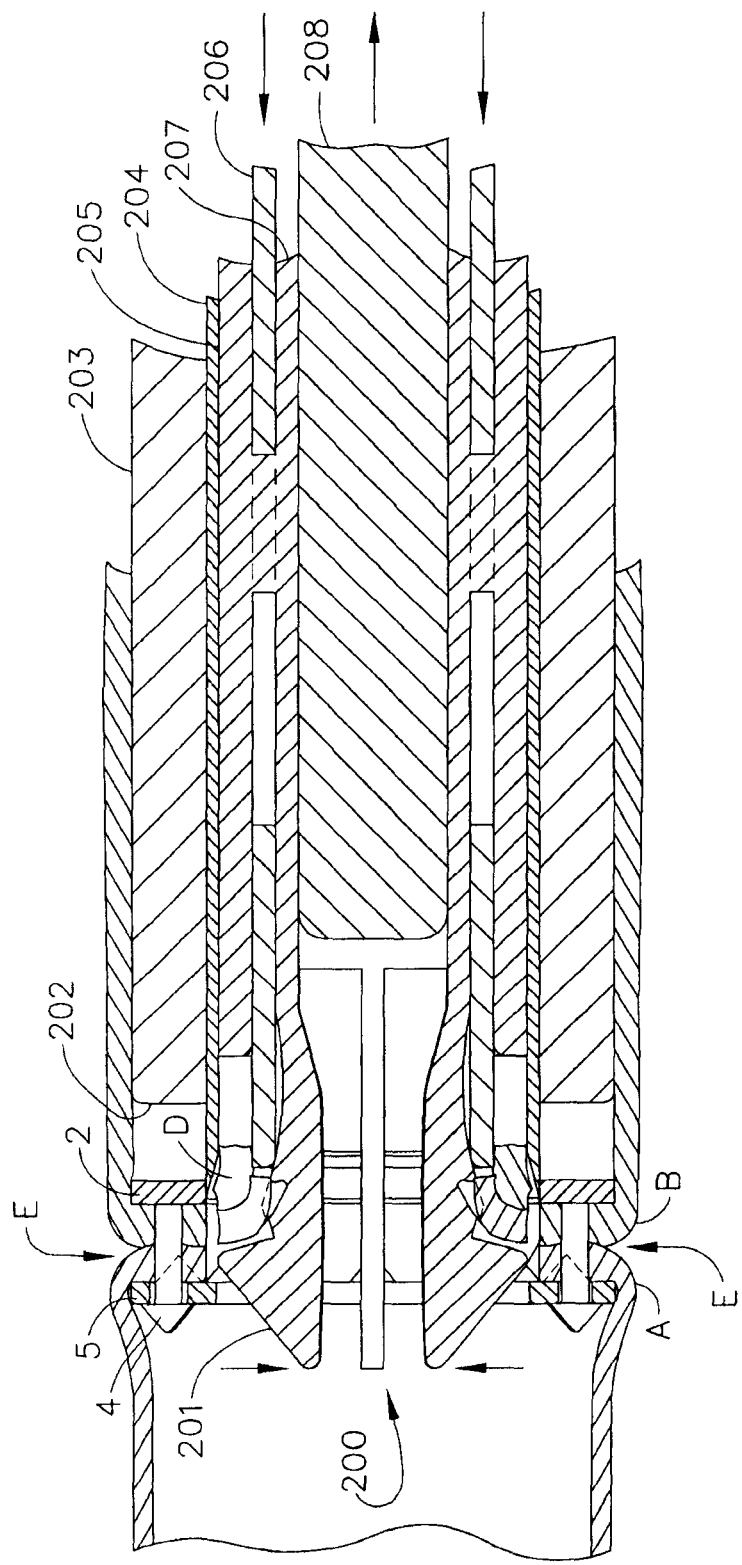
FIG. 26 is a longitudinal cross sectional view of the fastening ring applier shown in FIG. 21, shown in place within respective severed ends of hollow organ structures, following actuation to effect a connecting thereof, and following retraction of finger portions thereof to effect a release of fastening rings and enable withdrawal of the applier from the connection site.

Use and operation of the exemplary fastening ring applier 200 and exemplary fastener comprising fastening rings 2, 5 will now be described. Referring to FIG. 23, the distal portions of fingers 201 of fastening ring applier 200 may be inserted into one of the hollow organ structures at a remote location and guided therealong until it reaches severed end B. Thereafter, it may be guided into severed end A of the other structure or alternatively, severed end A may be guided over fingers 201, until severed ends A and B and fastening ring applier 200 are substantially in the positions illustrated in FIG. 23. The surgeon may elect to gather and tie ends A and B about fingers 201 using suture or other suitable material to create ties C as shown. Next, referring to FIG. 24, a proximally located and connected mechanism (not shown) may be actuated to cause seat tube 203 and thus seat 202 to move distally with respect to the rest of the assembly, urging proximal fastening ring 2 toward distal fastening ring 5 and driving connecting members 3 through the lips of respective ends A and B and into holes 4 in distal fastening ring 5, engaging the rings and drawing the tissues of ends A and B together to create connection site E. Alternatively, fingers 201 may be drawn toward seat 202, or fingers 201 and seat 202 may be simultaneously drawn and urged together, to effect the same result. Next, referring to FIG. 25, cutter tube 204 may be advanced distally with respect to the assembly, such that the sharpened distal end thereof is urged toward the inner facing surface of distal fastening ring 5. As the sharpened distal end of cutter tube 204 advances toward distal fastening ring 5, it will cut and sever excess tissue D from the lips of ends A and B, leaving a neat internal connection of the hollow organ structures. Following this severing, spreader 208 may be moved in a proximal direction with respect to the assembly, which will allow flexible fingers 201 to flex laterally, radially inward under urging of retractor tube 206 as it is moved in a distal direction with respect to the assembly, as shown in FIG. 26. When fingers 201 are moved radially inward, they clear the inner circumferences of fastening rings 2, 5, allowing the entire assembly to be withdrawn proximally, taking with it the severed tissue D and leaving behind installed fastening rings 2, 5, which maintain a connection of respective ends A and B at connection site E.

Figure 24:
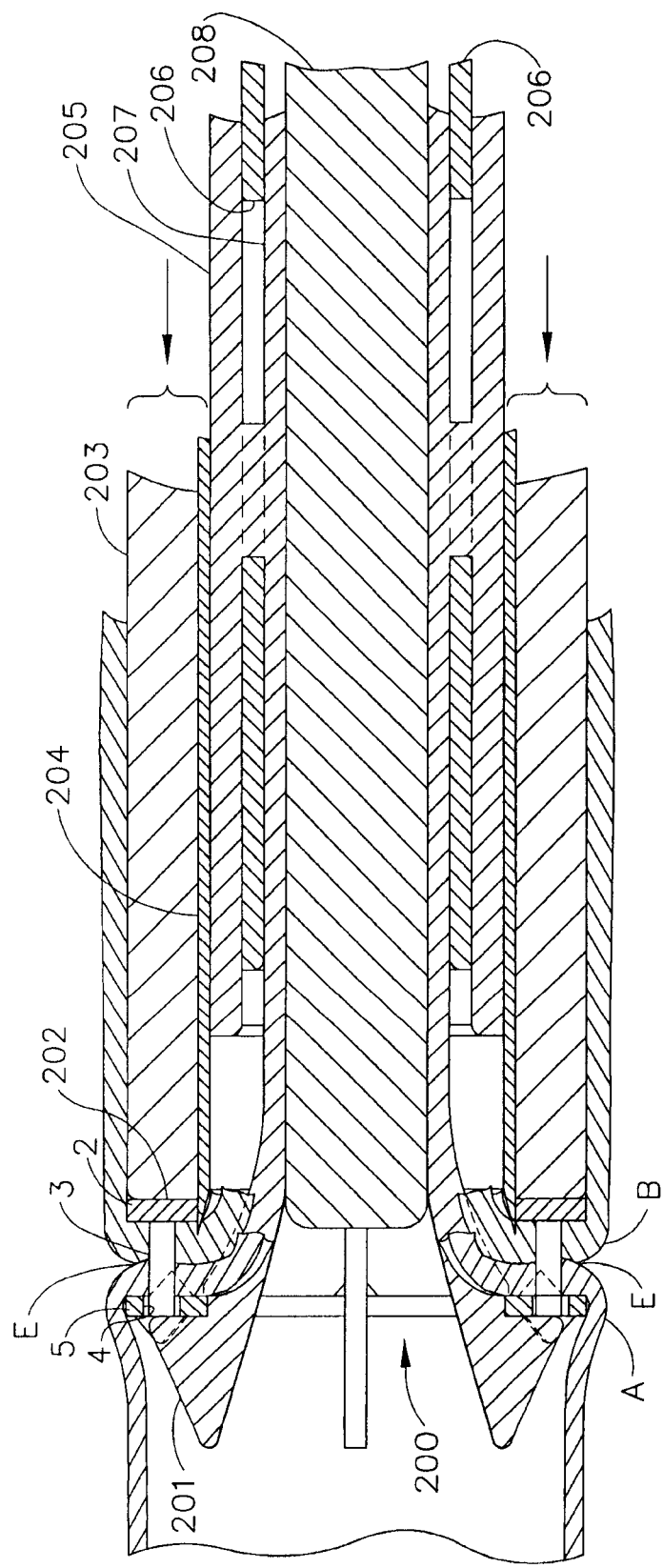
FIG. 24 is a longitudinal cross sectional view of the fastening ring applier shown in FIG. 21, shown in place within respective severed ends of hollow organ structures, following actuation to effect a connecting thereof.
Figure 25:
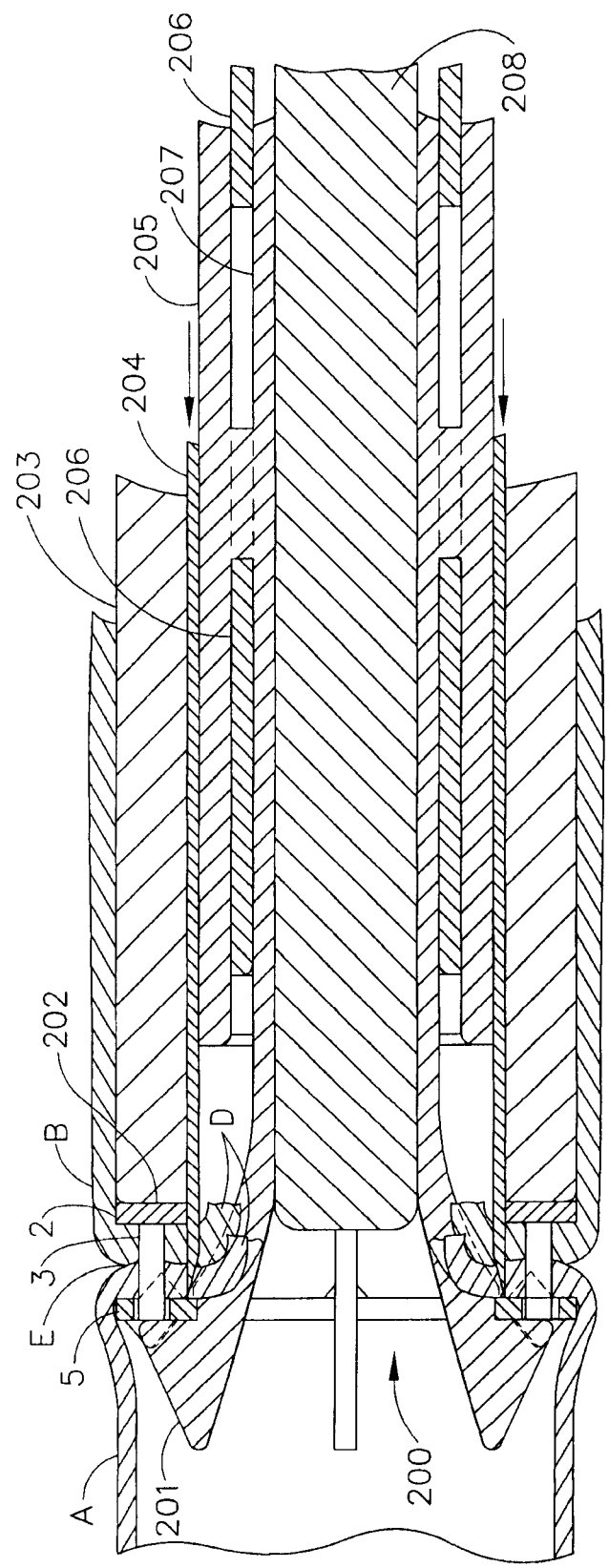
FIG. 25 is a longitudinal cross sectional view of the fastening ring applier shown in FIG. 21, shown in place within respective severed ends of hollow organ structures, following actuation to effect a connecting thereof, and following advancement of a cutter.

It will be appreciated that fastening rings 2, 5 may be suitably sized so that the outermost circumferences and/or diameters of rings 2, 5 approximately match or exceed the relaxed innermost circumference and/or diameter of the hollow organ structures at the connection site, so that obstruction to the passage of material moving through the hollow organ structures, caused by the presence of installed fastening rings 2, 5 is minimized. It also will be appreciated that, with some organ structures such as, for example, intestines or other hollow organs having annular muscle structures, when the outer diameters and/or circumferences of internally placed members such as fastening rings 2, 5 exceed the relaxed inner circumferences and/or diameters of the hollow organ structures proximate to the connection site, the structures at the overhanging portions of severed ends A and B will tend to retain their relaxed innermost circumferences and/or diameters, or contract, as conceptually illustrated in FIG. 23, facilitating the capture of the lips of ends A and B between fastening rings 2, 5, as shown in FIG. 24. Thus, fastening rings 2, 5 may be suitably sized and formed to take advantage of this phenomenon.

The fastening rings 2, 5 also may be continuous or discontinuous, for example, either may comprise split ring structures; either may be made so as to form only a partial, or alternatively, a complete and continuous, ring; and either may have any suitable cross section and any suitable shape (i.e., it need not necessarily be circular or round, but may have, for example, an oval shape, a "C", "D" or "U" shape, or other suitable shape).

In the example shown, fastening rings 2, 5 may comprise any suitable biocompatible and/or bioabsorbable material, including adhesive or initiator materials that are activated and commence curing or setting after placement and connecting of the respective ends A and B. For example, one of fastening rings 2, 5 or connecting members 3 may comprise an initiator, and the other ring may comprise an adhesive. When the rings are brought together, curing or setting will commence. Alternatively, fastening rings 2, 5 may comprise hollow, porous or matrix structures and may contain or be impregnated with adhesive and/or initiator, that are released and placed in contact to induce flow about the connection and setting or curing when rings 2, 5 are compressed. Fastening rings 2, 5 may also be formed of one or more suitable bioabsorbable and/or degradable materials, selected such that they will break apart and/or dissolve within a suitable period of time after installation, e.g. after a period of time sufficient for ends A and B to heal together. Such components can break apart and/or dissolve so as can be swept out of the patient's system through bodily functions, e.g. through passage of chyme material through the intestinal tract, leaving the internal passage past the connection site clear of potential obstruction created by the presence of installed objects.

The respective facing proximal and distal faces of fastening rings 2, 5, and connecting members 3, may be formed and/or sized to accommodate the wall thickness of the hollow organ structures to be connected; additionally, these faces may have any suitable features formed to enhance gripping of tissues between them, affect the shape or configuration of the connection site, and/or enhance and/or restrict circulation within the fastened tissues, e.g. to prevent and/or intentionally cause necrosis. Such features may include but are not necessarily limited to cooperating undulations, piercing or partially piercing features such as teeth or other projections, circumferential offset, mating, abutting or cooperating ridges, edges, projections, holes, slots, depressions and/or grooves, and any other suitable features.

Alternatively or in addition, use of fastening rings 2, 5 as a fastener could be made in conjunction with buttress rings 20, 21 or beads 30, 31 in the manner described above and depicted in FIGS. 14-19.

Following installation of fastening rings 2, 5 to connect respective severed ends of hollow organ structures A and B as described above, the connection site may be covered by a protective wrap and adhesive combination in the manner described above and depicted generally in FIGS. 4 and 5, the only difference being that a fastener comprising fastening rings 2, 5 performs the tissue holding and fastening function rather than another type of fastener depicted in, for example, FIGS. 3, 4, 6-8, 10-14, 15, 16 and 18-20.

Figure 27:
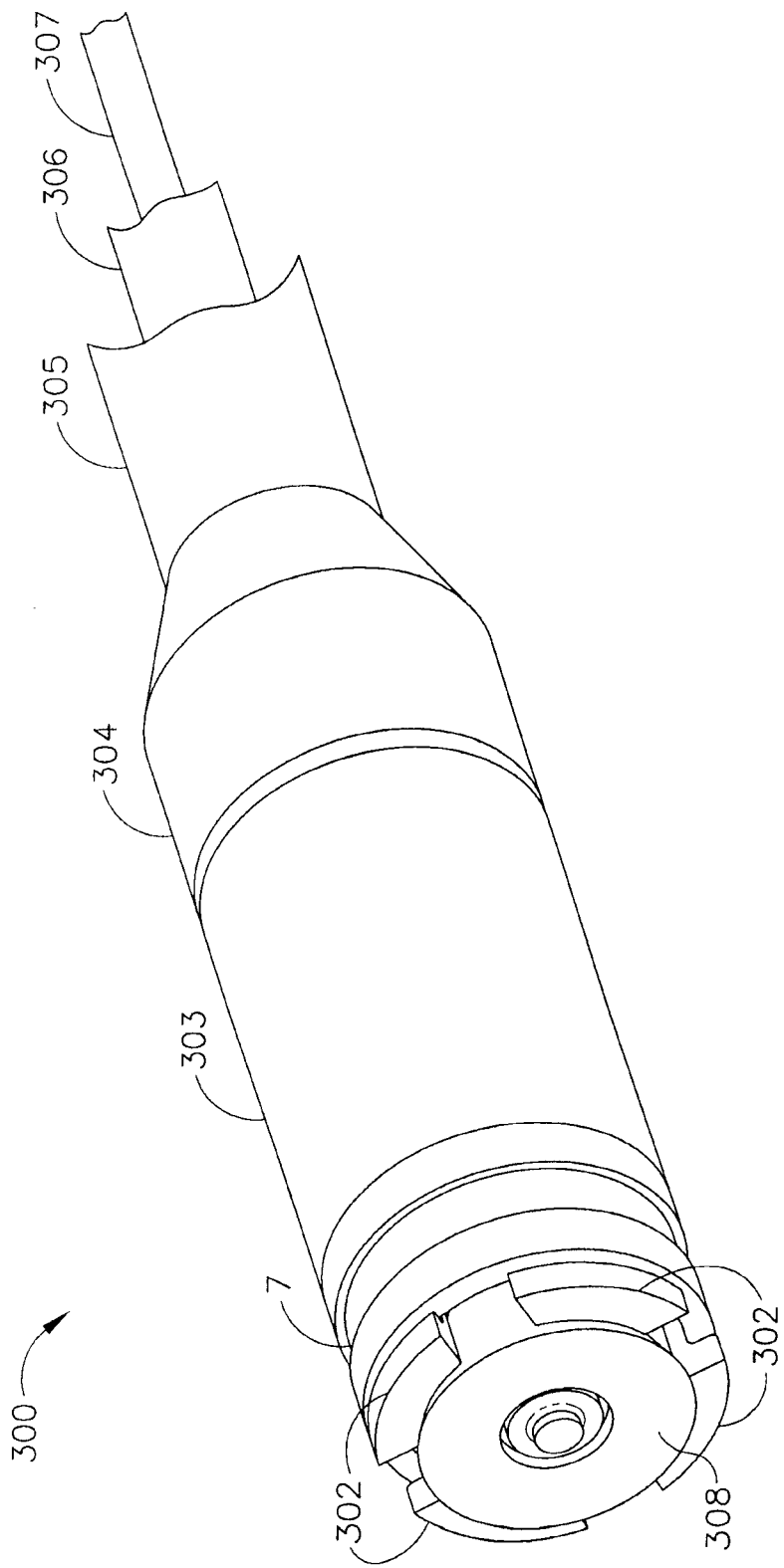
FIG. 27 is a perspective view of a circumferential fastener applier with a circumferential fastener loaded thereon.
Figure 28:
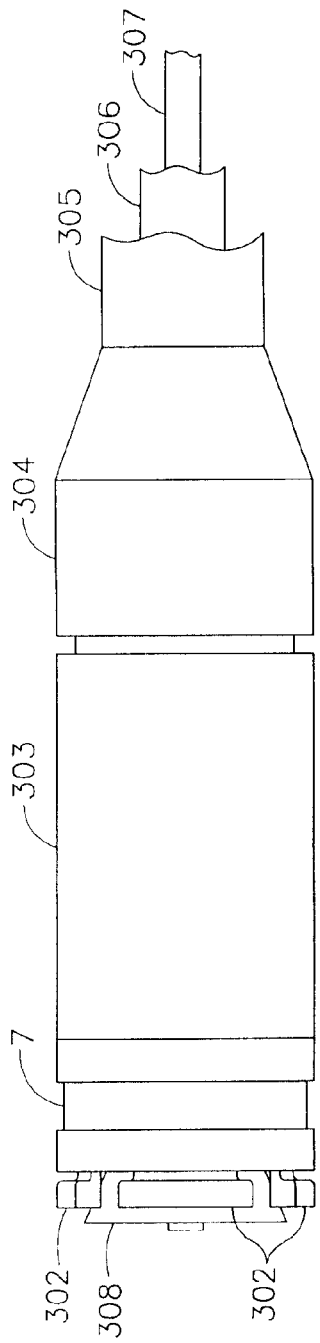
FIG. 28 is a side view of the applier shown in FIG. 27.
Figure 29:
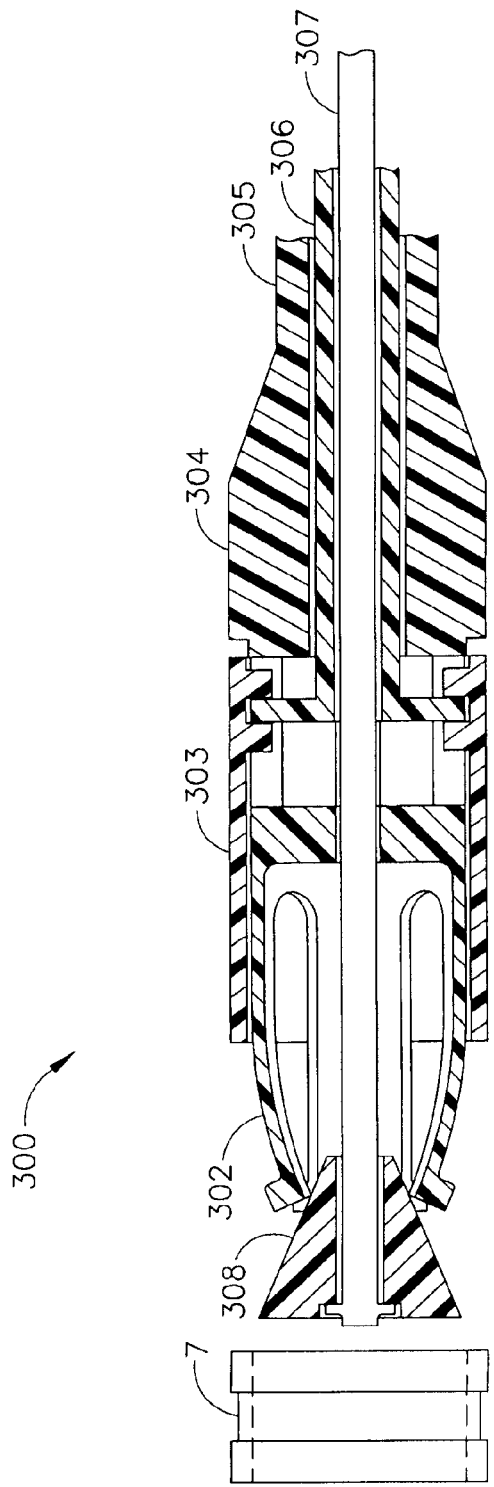
FIG. 29 is a longitudinal cross sectional view of the applier and fastener shown in FIG. 27, prior to loading of the fastener onto the applier.
Figure 30:
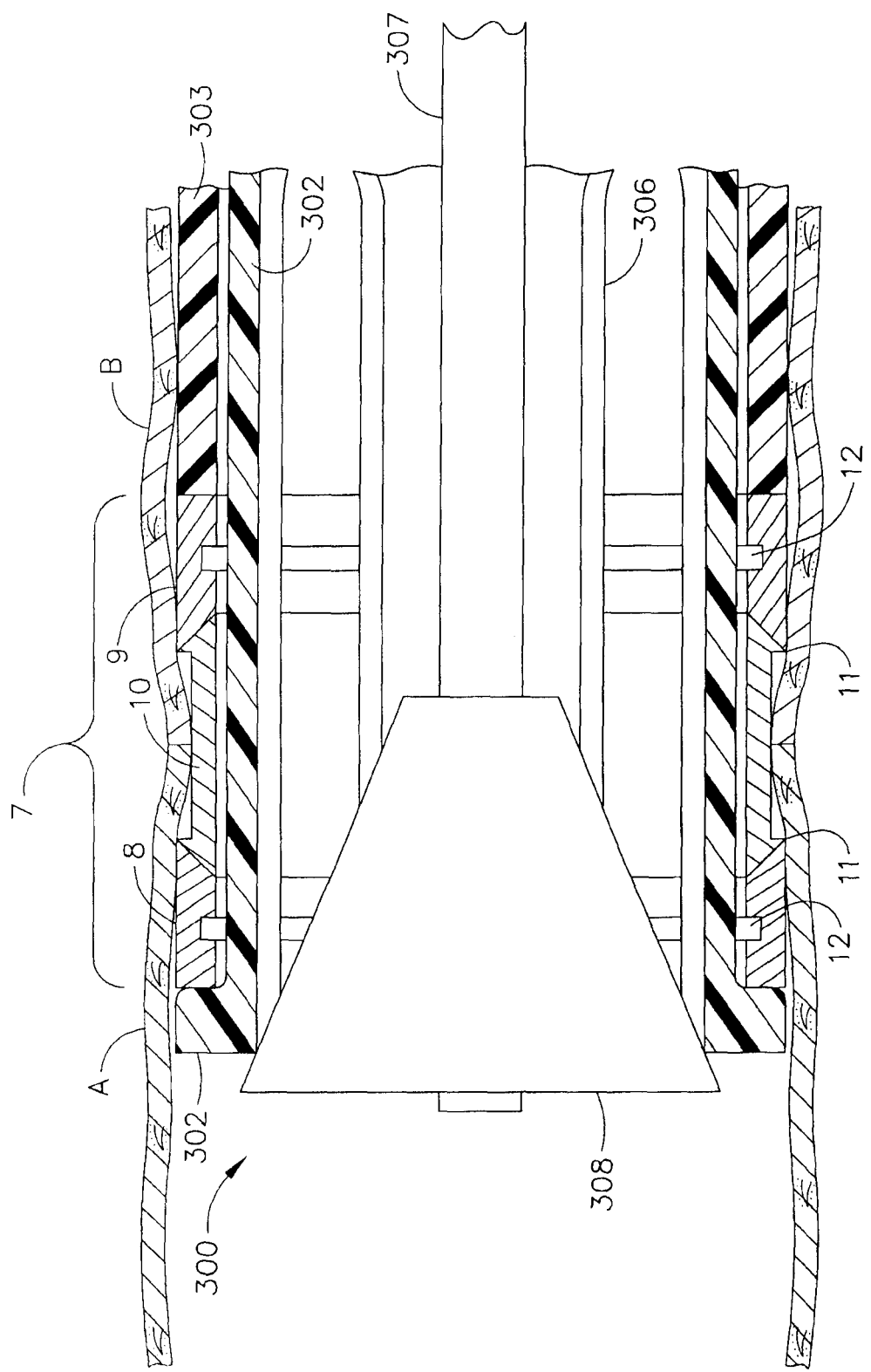
FIG. 30 is a longitudinal cross sectional view of the distal end of the applier shown in FIG. 27, shown in position ready to be actuated to connect respective severed ends of hollow organ structures.

FIGS. 27-33 depict another alternative example of a combination of devices and method for accomplishing anastomosis of respective severed ends of hollow organ structures A and B. Referring to FIGS. 27, 28 and 30, circumferential fastener applier 300 may comprise a circumferential fastener 7, held at the distal end of the device between ledges at the distal ends of fingers 302 and compressor cup 303. Fingers 302 may be connected to base 304, which is held by support tube 305. Compressor cup 303 may be connected with compressor rod 307 and move longitudinally in conjunction therewith with respect to base 304 and fingers 302. The proximal portion of spreader 308, which may have a conical or other suitable shape, may be attached to spreader rod 307 and moves longitudinally in conjunction therewith with respect to base 304 and fingers 302. The distal surface of spreader 308 may be flat as shown, or may be, e.g. hemispherical or bullet-shaped to facilitate insertion into and along the passageway of a hollow organ structure, or have any other suitable shape. Respective tubes 305 and 306, and spreader rod 307, may be held and longitudinally moved with respect to each other to effect operation as will hereinafter be described, by any suitably connected structure and mechanism located proximally of the applier.

FIG. 29 depicts the applier 300 before circumferential fastener 7 has been loaded thereon. Fingers 302 may be made so as to be flexible and elastic, with a bias such that their distal ends tend to move laterally, radially inward when not held in an outwardly spread position by a member such as spreader 308. Thus, in the example shown, when spreader rod 307 is moved distally with respect to base 304 and fingers 302, the distal ends of fingers 302 are permitted to move laterally, radially inward such that the ledges thereof clear the inner diameter of circumferential fastener 7. This will allow circumferential fastener 7 to be loaded longitudinally over fingers 302, to a position abutting the distal end of compressor cup 303. Thereafter, spreader rod 307 may be retracted proximally, pulling spreader 308 proximally, which in turn urges fingers 302 laterally radially outwardly, whereby the ledges thereof retain circumferential fastener 7 in place on the applier as shown in FIGS. 27 and 28.

In the example of a fastener shown, circumferential fastener 7 may have three components: distal clamp ring 8, proximal clamp ring 9, and expander ring 10 (see, e.g. FIG. 30, components of fastener 7 shown in longitudinal cross section). Expander ring 10 supports clamp rings 8, 9 in substantially coaxial relationship to one another. The distal and proximal edges of expander ring 10 may be angled as shown. In conjunction or as an alternative, the distal and proximal ends of proximal clamp ring 9 and distal clamp ring 8, respectively, also may be angled as shown. Additionally, distal and proximal clamp rings 8, 9 may be elastically circumferentially deformable so as to be expandable/stretchable by any suitable mechanism, such as by having a serpentine construction, by comprising a discontinuous coiled or split ring member rather than a continuous ring, or by comprising an elastic stretchable material. Alternatively, a band (not shown) made of elastic material may be included to wrap around the outer circumferential surfaces of fastener 7 and apply circumferential and inwardly radial tension/pressure against the outer surfaces and/or provide a smooth outer surface of fastener 7. Any of distal and proximal clamp rings 8, 9 and expander ring 10 may be continuous or discontinuous, for example, it may be a split ring; it may be made so as to form only a partial, or alternatively, a complete and continuous, ring; and it may have any suitable cross section and any suitable shape (i.e., it need not necessarily be circular or round, but may have, for example, an oval shape, a "C", "D" or "U" shape, or other suitable shape). Distal and proximal clamp rings 8, 9 may have locking grooves 12 around the inner circumferences thereof. The angled portions of expander ring 10 may have radially projecting ridges 11 formed to fit within locking grooves 12 of clamp rings 8, 9 when the fastener is installed as will be described below. The respective facing proximal and distal edges, i.e., clamping edges, of clamp rings 8, 9 may be formed and/or sized to accommodate the wall thickness of the hollow organ structures to be connected; additionally, these edges may have any suitable features formed to, e.g. enhance gripping of tissues between them, affect the shape or configuration of the connection site, and/or enhance and/or restrict circulation within the fastened tissues, e.g. to prevent and/or intentionally cause necrosis. Such features may include but are not necessarily limited to cooperating undulations, piercing or partially piercing features such as teeth or other projections, circumferential offset, mating, cooperating or abutting ridges, edges, projections, holes, slots, depressions and/or grooves, and any other suitable features. The components of fastener 7 may also be formed of one or more suitable bioabsorbable and/or degradable materials, selected such that the components will break apart and/or dissolve within a suitable period of time after installation, e.g. after a period of time suitable to allow ends A and B to heal together. Such components can break apart and/or dissolve so as can be swept out of the patient's system through bodily functions, e.g. through passage of chyme material through the intestinal tract, leaving the internal passage past the connection site clear of potential obstruction created by the presence of installed objects.

Figure 31:
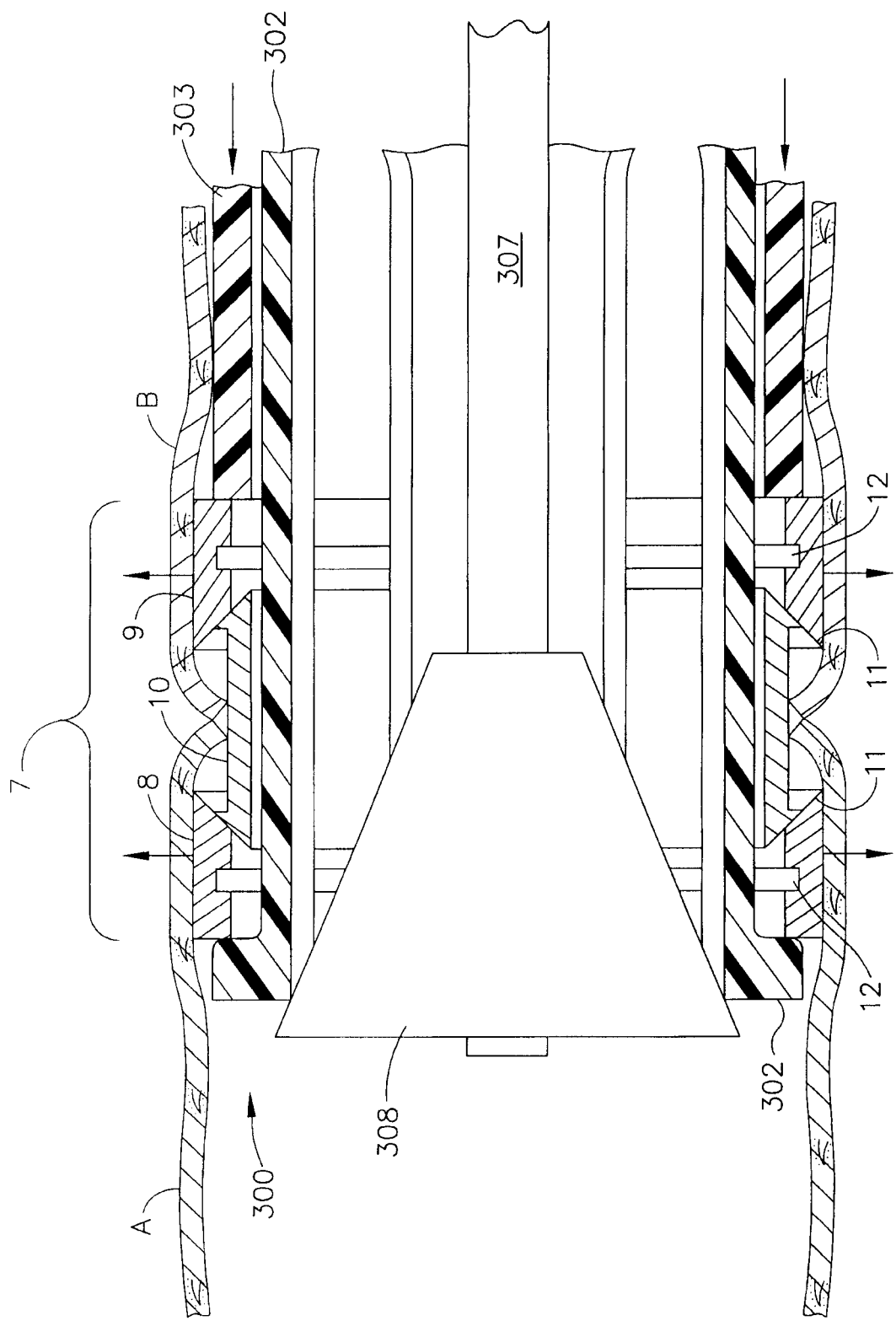
FIG. 31 is a longitudinal cross sectional view of the distal end of the applier shown in FIG. 27, shown in position to connect respective severed ends of hollow organ structures, after actuation has commenced.

Use and operation of the exemplary circumferential fastener applier 300 and exemplary fastener 7 will now be described. Referring to FIG. 30, the distal end of applier 300 may be inserted into one of the hollow organ structures at a remote location and guided therealong until it reaches severed end B. Thereafter, it may be guided into severed end A of the other respective structure or alternatively, severed end A may be guided over the distal end of applier 300, until severed ends A and B and applier 300 are substantially in the positions illustrated in FIG. 30. Next, a proximally located mechanism (not shown) may be actuated to cause compressor tube 306 and thus compressor cup 303 to move longitudinally distally with respect to fingers 302, thereby longitudinally compressing circumferential fastener 7. Longitudinal compression of fastener 7 will force clamping rings 8, 9 to ride radially out and longitudinally over the angled surfaces of expander ring 10 as shown in FIG. 31, and force clamping rings 8, 9 to expand or stretch circumferentially. Continued longitudinal compression of fastener 7 in this manner will cause the inner surfaces of clamping rings 8, 9 to ride over the tops of ridges 11 of expander ring 10 until ridges 11 snap into locking grooves 12 in clamping rings 8, 9, to the position shown in FIG. 32. It can be seen that when fastener 7 has been longitudinally compressed to the position shown in FIG. 32, clamping rings 8, 9 clamp respective lips of ends A and B together, forming a connection thereof Following the installation of circumferential fastener 7 and establishment of a connection of ends A and B in this manner, the surgeon may actuate the applier so as to move spreader 308 longitudinally distally with respect to fingers 302, allowing fingers 302 to move laterally inwardly under their bias (see, e.g. FIG. 29), clearing the inner diameter of circumferential fastener 7. Thus, the applier may be withdrawn, leaving the installed circumferential fastener 7 in place connecting the hollow organ structures as shown in FIG. 33.

It will be appreciated that fastener 7 may be suitably sized so that the outermost circumference and/or diameter of fastener 7 approximately matches or exceeds the relaxed innermost circumference and/or diameter of the hollow organ structures at the connection site, so that obstruction to the passage of material moving through the hollow organ structures, caused by the presence of installed fastener 7, is minimized. It also will be appreciated that, with some organ structures such as, for example, intestines or other hollow organs having annular muscle structures, when the outer diameters and/or circumferences of internally placed members such as clamping rings 8, 9 exceed the relaxed inner circumferences and/or diameters of the hollow organ structures proximate to the connection site, the structures at the overhanging portions of severed ends A and B will tend to retain their relaxed innermost circumferences and/or diameters, or contract, as conceptually illustrated in FIGS. 30 and 31, facilitating the capture of the lips of ends A and B between clamping rings 8, 9, as shown in FIG. 32. Thus, fastener 7 and/or clamping rings 8, 9 may be suitably sized and formed to take advantage of this phenomenon.

Alternatively or in addition, use of circumferential fastener 7 may be made in conjunction with buttress rings 20, 21 or beads 30, 31 in the manner described above and depicted in FIGS. 14-19.

Following installation of circumferential fastener 7 to connect respective severed ends of hollow organ structures A and B as described above, the connection site E may be covered by a protective wrap and adhesive or initiator combination in the manner described above and depicted generally in FIGS. 4 and 5, the only difference being that circumferential fastener 7 performs the tissue holding and fastening function rather than the other types of fasteners depicted in, for example, FIGS. 3, 4, 6-8, 10-14, 15, 16, 18-20, and 21-26.

At a connection site E created by installation of any fasteners such as those shown in, for example, FIGS. 3, 6, 13, 15, 19, 26 and 33, the surgeon also may deposit an adhesive about the connection site to directly adhere the respective tissues, supplement connection site holding force and/or provide improved sealing of the connection site. This can produce a deposit of adhesive 13 about the connection site such as depicted in FIG. 19, and may be done in conjunction with and supplement to, or in lieu of, use of a wrap 50 as depicted in, for example, FIGS. 4, 16 and 20.

From the foregoing it will be appreciated that use of various combinations of fasteners in conjunction with adhesives and/or wrapping and/or buttressing members may be employed to facilitate establishing a leak-free connection between respective openings in hollow organ structures, and effecting a successful anastomosis thereof. Thus, it will be appreciated that the embodiments disclosed and described herein are only examples of a greater number of possible embodiments of methods and devices that may be constructed and utilized to attain the benefits and advantages described herein. Accordingly, the scope of the invention is limited only by the claims appended hereto, and equivalents thereof.

We claim:

1. A method for effecting an anastomosis of a first and second hollow tubular organ structure, each hollow tubular organ structure having a severed end and an outside perimeter that defines a lumen in each hollow tubular organ structure, the method comprising:
   placing a bead of material comprising adhesive around an edge of the severed end of the first hollow tubular organ structure;
   placing a bead of material comprising adhesive initiator around an edge of the severed end of the second hollow tubular structure;
   bringing the severed ends of said hollow tubular organ structures together such that the beads of material of said first and second hollow tubular organ structure meet to form an adhesive deposit and seal the connection of said first and second hollow tubular organ structures;
   providing at least one transformable fastener, wherein the at least one transformable fastener comprises a pair of deformable ends operably configured to hold said hollow tubular organ structures together;
   providing an applier operable to apply said at least one transformable fastener, wherein the applier comprises:
      a first fastener transforming member having a first surface, wherein the first fastener transforming member contacts one of the pair of deformable ends of the at least one transformable fastener;
      a second fastener transforming member having a second surface, wherein the second fastener transforming member contacts another one of the pair of deformable ends of the at least one transformable fastener; and
      a mechanism holding said first fastener transforming member and said second fastener transforming member in operable positions with respect to each other;
   wherein said mechanism may be actuated so as to cause said first surface to move toward said second surface, and during actuation said first and second surfaces exert at least partially opposing forces that cause transformation of said at least one transformable fastener such that the deformable ends face away from the longitudinal axis of the applier;
   using said applier to apply said at least one transformable fastener to hold the severed ends of said hollow tubular organ structures together resulting in a connection of the severed ends and merging of the beads of material, thereby forming a connection site where said two hollow tubular organ structures are held together; and
   placing a wrap comprising a hydrophilic material, a therapeutic material, and a dry adhesive over at least a portion of said connection site, wherein the dry adhesive is configured to be activated by one or both of contact with water drawn from the tissues or an initiator applied by a user and wherein the dry adhesive comprises a 1,1-disubstituted ethylene monomer.

2. The method of claim 1 wherein said wrap further comprises a material selected from the group consisting of an accelerator and an additive.

3. The method of claim 1 wherein said at least one transformable fastener comprises a material selected from the group consisting of a bioabsorbable material and a degradable material.

\* \* \* \* \*